United States Patent
Woldt et al.

(10) Patent No.: US 10,421,850 B2
(45) Date of Patent: Sep. 24, 2019

(54) PENTYL NONYL TEREPHTHALATES

(71) Applicants: Benjamin Woldt, Bochum (DE); Florian Sebastian Boeck, Muenster (DE); Michael Grass, Haltern am See (DE); Harald Haeger, Luedinghausen (DE)

(72) Inventors: Benjamin Woldt, Bochum (DE); Florian Sebastian Boeck, Muenster (DE); Michael Grass, Haltern am See (DE); Harald Haeger, Luedinghausen (DE)

(73) Assignee: Evonik Degussa GmbH, Essen (DE)

( * ) Notice: Subject to any disclaimer, the term of this patent is extended or adjusted under 35 U.S.C. 154(b) by 3 days.

(21) Appl. No.: 15/046,242

(22) Filed: Feb. 17, 2016

(65) Prior Publication Data

US 2016/0237243 A1    Aug. 18, 2016

(30) Foreign Application Priority Data

Feb. 18, 2015   (EP) ..................................... 15155562

(51) Int. Cl.
| | |
|---|---|
| *C08K 5/12* | (2006.01) |
| *C08L 27/06* | (2006.01) |
| *C07C 67/03* | (2006.01) |
| *C07C 67/08* | (2006.01) |
| *C07C 69/82* | (2006.01) |

(52) U.S. Cl.
CPC ............... *C08K 5/12* (2013.01); *C07C 67/03* (2013.01); *C07C 67/08* (2013.01)

(58) Field of Classification Search
USPC ...................................... 524/296, 297; 560/1
See application file for complete search history.

(56) References Cited

U.S. PATENT DOCUMENTS

| | | | | |
|---|---|---|---|---|
| 4,100,325 | A * | 7/1978 | Summers | ................ B32B 27/08 428/334 |
| 6,559,213 | B2 * | 5/2003 | Wesch | .................... B60R 13/08 524/296 |
| 9,127,141 | B2 * | 9/2015 | Lee | .......................... C08K 5/12 |
| 2007/0179229 | A1 | 8/2007 | Grass | |
| 2009/0288359 | A1 * | 11/2009 | Martin, Jr. | ........... C08K 5/0016 52/309.1 |
| 2014/0096703 | A1 | 4/2014 | Lee et al. | |
| 2014/0336294 | A1 | 11/2014 | Kim et al. | |
| 2014/0336320 | A1 | 11/2014 | Lee | |

FOREIGN PATENT DOCUMENTS

| | | |
|---|---|---|
| WO | 2008140177 A1 | 11/2008 |
| WO | WO 2008/140177 A1 | 11/2008 |
| WO | WO 2014/195055 A1 | 12/2014 |

OTHER PUBLICATIONS

European Search Report dated Aug. 10, 2015, in U.S. Appl. No. 15/155,562 (with English translation of categories of cited documents).

* cited by examiner

*Primary Examiner* — Tae H Yoon

(74) *Attorney, Agent, or Firm* — Oblon, McClelland, Maier & Neustadt, L.L.P.

(57) ABSTRACT

Mixtures containing dipentyl terephthalate, dinonyl terephthalate and pentyl nonyl terephthalate can be prepared with a predetermined distribution of the individual esters in the mixture, and used as plasticizers.

8 Claims, 2 Drawing Sheets

10,421,850 B2

PENTYL NONYL TEREPHTHALATES

CROSS REFERENCE TO RELATED APPLICATIONS

This application claims priority to European patent application EP15155562 filed Feb. 18, 2015, which is incorporated herein by reference in its entirety.

BACKGROUND OF THE INVENTION

Field of the Invention

The present invention relates to mixtures of terephthalic esters, to preparation processes and uses of such mixtures as plasticizer, and to compositions which comprise such mixtures.

Discussion of the Background

Within the area of the plasticizers for polymers, terephthalic esters have already been used for a number of years as a replacement for or supplemented to phthalic esters. The most important terephthalic ester commercially has for years been diethylhexyl terephthalate, which is often also referred to, in simplified form, as dioctyl terephthalate. Terephthalic esters which comprise alcohol radicals having fewer or more than 8 carbon atoms are likewise described in the related art.

Dependent on factors including the number of carbons in the alcohol radicals of the ester functions, the terephthalic esters have different properties and are suitable accordingly to a greater or lesser extent for different plasticizer applications. For instance, relatively short-chain terephthalic esters tend to gel at lower temperatures than their longer-chain homologues. A low gelling temperature in a plasticizer represents a positive property in the context of plastisol processing, since this processing can be carried out at lower temperatures and, moreover, higher processing throughputs can be achieved than in the case of the processing of plastisols which comprise plasticizers having a high gelling temperature. At the same time, however, terephthalic esters with a low molecular weight and accordingly, a low number of carbons in the alcohol radical have a higher volatility than their heavier homologues. High volatility in a plasticizer is a serious disadvantage, since plasticized loss not only alters the properties of plasticized polymer and hence reduces the longevity of the product but also releases plasticizer into the environment.

This release of plasticizer is a problem, moreover, since in the fields of interior applications, medical products, toys, cables and in the automobile sector, for example, marketing of the products requires compliance with standards which govern parameters including the maximum amount of organic compounds emerging from a product, in order to ensure the necessary safety for consumers and the environment. Thus, for example, in Germany, the construction products Health Evaluation Committee (AgBB), in harmony with the Construction Products Regulation (No. 305/2011) agreed by the European Parliament, regulates the avoidance and limitation of pollutants in interior spaces. From a health standpoint, accordingly, construction products, and hence also plasticizer-containing products, are deemed suitable for use in interior spaces in buildings only when certain limit values for emitted VOCs (Volatility Organic Compounds) and SVOCs (Semi-volatile Organic Compounds) are not exceeded in a standardized measurement process. In accordance with DIN ISO 16000-6, organic compounds classed as SVOCs are those which are situated in the retention range of >C16-C22 on a nonpolar column (AgBB—Evaluation Scheme for VOC from construction products, 2012 status). Products which have higher-than-permitted emissions of VOCs and/or SVOCs can be used only when additional measures, such as the application of an emission barrier layer of varnish, for example, prevent the maximum-permitted emissions quantity being exceeded. The necessity for such additional measures, however, restricts the freedom in the formulation of the plasticizers in products and therefore makes it more expensive to use plasticizers having an SVOC classification. Moreover, as a result of the necessity for such additional protective coats, further difficulties may arise, such as, for example, increased susceptibility of a varnish-protected, SVOC-containing product to scratches or flaking.

In order to adjust the properties of the plasticizer system to the conditions of the processing and to the planned application, it is common to use mixtures of two or more plasticizers, for example two terephthalic diesters having different alcohol radicals, as plasticizers for polymers. Accordingly, document US 2013/0317152 A1 proposes using diisononyl terephthalate in a mixture with other terephthalic dialkyl esters, preferably those having 4 to 8 carbon atoms in the alcohol radical. Document US 2013/0310473 A1 as well describes plastisols which as well as dinonyl terephthalate also comprise di-n-butyl terephthalate. Through use of mixtures of two or more plasticizing substances (also called plasticizers) to form a plasticizer mixture, often likewise referred to, in simplified form, as plasticizer, success has hitherto not been achieved, however, in custom-tailoring all of the desirable combinations of advantageous properties. For example, the document "Dibutyl terephthalates in Plasticizer and related Applications" (IP.com, publication number: IPCOM000236730D, publication date: 13 May 2014) discloses polymer compatibility problems affecting mixtures of different terephthalic esters. For instance, FIG. 8 in this document shows that dioctyl terephthalate has sufficient polymer compatibility only in a mixture with more than 50% of dibutyl terephthalate. Systems comprising dioctyl terephthalate and dibutyl terephthalate, therefore, only did not exude from the polymer if they contained more than 50% of dibutyl terephthalate; this severely limits the range for variation of the mixture compositions and hence also greatly restricts the properties which can potentially be achieved.

Other documents proposed not only blending different terephthalic diesters but also using the two terephthalic diesters together with the associated mixed ester as plasticizers.

Accordingly, documents KR 2013/0035493 A and US 2014/0336294 A1 set out the problem that dibutyl terephthalate, while exhibiting a high rate on penetration into the resin and on melting, nevertheless exhibited an undesirably high migration loss, whereas in the case of diethylhexyl terephthalate there was virtually no migration loss, but penetration into the resin and melting took an unacceptably long time. In order to improve these contrary properties, these documents propose using ester mixtures comprising mixed esters containing a $C_4$ and a $C_8$ alcohol radical. These ester mixtures, however, have the disadvantage that they include terephthalic dibutyl esters, which are classified as a SVOC component and whose use is subject accordingly to the above-described restrictions in formulation.

Document WO 2008/140177 A1 proposes the preparation of ester mixtures comprising $C_8$ and $C_9$ esters of terephthalic acid, again including the mixed ester as well, and describes the possibility of achieving an improvement in the processing properties of the plasticizer preparations by varying the proportions of the individual esters in the ester mixture.

Relative to these terephthalic ester mixtures of the $C_8$ and $C_9$ esters, however, according to document US 2014/0096703 A1, terephthalic ester mixtures comprising $C_8$ and $C_{10}$ esters also had significantly improved properties. The systems proposed in this document comprise mixed esters containing a $C_8$ and a $C_{10}$ alcohol radical, but their compatibility with polymers was so poor that the document itself proposes admixing the phthalate plasticizer dipropylheptyl phthalate to the terephthalic ester mixture in order to improve the compatibility.

Document US 2014/0336320 A1, alongside systems which include $C_4$ and $C_8$ terephthalic esters, also proposes those with $C_8$ and $C_{10}$ alcohol radicals.

Document WO 2014/195055 A1 describes not only terephthalic ester mixtures with $C_8$ and $C_{10}$ alcohol radicals but also those with $C_7$ and $C_9$ alcohol radicals.

SUMMARY OF THE INVENTION

It was an object of the present invention, accordingly, to overcome some and preferably all of the above-stated disadvantages of the related art. The intention preferably was to provide a plasticizer which in order to ensure maximum freedom in formulation, does not fall within the definitions of the compounds regulated by German or international directives. The intention with preference here was to provide a plasticizer based on terephthalic esters that at the same time has good properties in the area of volatility and of gelling temperature, in other words a plasticizer which gels at low temperatures and is at the same time of low volatility.

These and other objects have been achieved by the present invention which relates to a mixture, comprising:

a terephthalic diester of each of the formulae I, II and III,

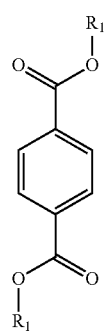

I

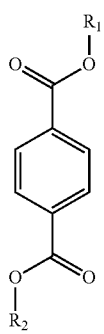

II

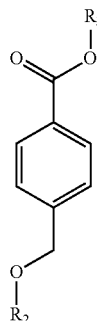

III wherein $R_1$ is an alkyl radical having 5 carbon atoms, and $R_2$ is an alkyl radical having 9 carbon atoms.

In another embodiment, the present invention relates to a polymer plasticizer, comprising:

the above mixture.

The present invention also relates to an adhesive, sealant, coating material, paint, ink, plastisol, foam, synthetic leather, floorcovering, roofing membrane, underbody protection, fabric coating, cable, wire insulation, hose, extruded article, film, automotive interior article, wallcovering, liquid ink, toy, contact sheet, food packaging or medical article, comprising:

the above polymer plasticizer.

The present invention relates to a composition, comprising:

a mixture as above; and one or more polymers selected from the group consisting of polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

The present invention also relates to a process for preparing an ester mixture as above, said process comprising:

esterifying terephthalic acid or a terephthalic acid derivative with a mixture comprising $R_1OH$ ($R_1$=alkyl radical having 5 carbon atoms) and $R_2OH$ ($R_2$=alkyl radical having 9 carbon atoms).

In another embodiment, the present invention relates to a process for preparing an ester mixture as above, said process comprising:

reacting the ester of formula I with less than 1 mole equivalent, based on the number of ester functions in the ester of formula I, of an alcohol or of two or more alcohols having 9 carbon atoms in a reaction mixture, while heating said reaction mixture.

Moreover the present invention relates to a process for preparing an ester mixture as above, said process comprising:

reacting terephthalic acid with a derivative of terephthalic acid which contains no ester group COOR with a radical R whose alcohol ROH has a higher boiling point at a defined pressure than the alcohol $R_1OH$ of the radical $R_1$ at the same pressure, with an amount $(m_1+s_1)$ of $R_1OH$ and an amount $m_2$ of $R_2OH$, the reaction mixture being heated at boiling, wherein $m_1$ and $m_2$ correspond to the mole equivalents of the alcohol radical $OR_1$ ($C_5$ alcohol radical) and $OR_2$ ($C_9$ alcohol radical) to be introduced into terephthalic acid or derivatives thereof, and $s_1$ is greater than 0.

DETAILED DESCRIPTION OF THE INVENTION

Figure 1:
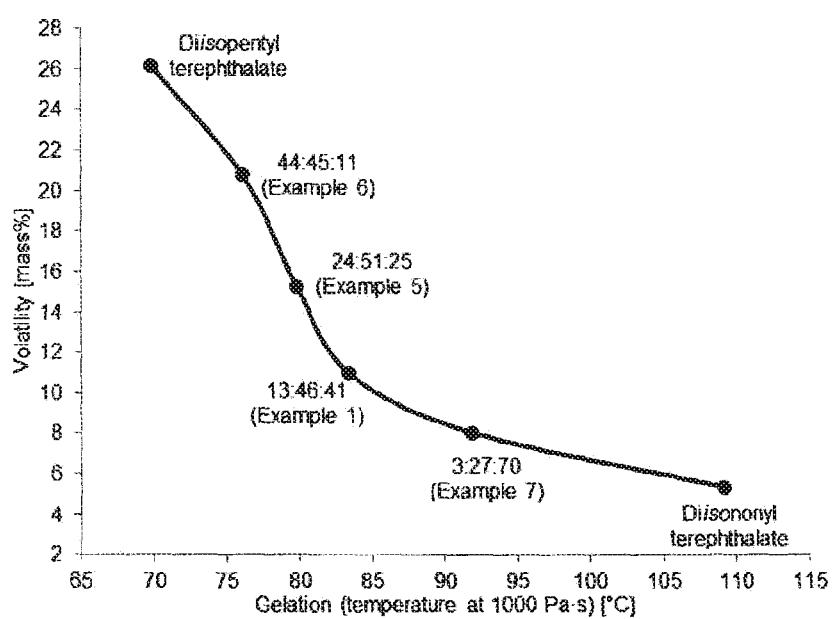
FIG. 1 shows a plot of gelling temperature against volatility for ester mixtures of various compositions (indicated at the data points is the associated molar ratio of diisopentyl terephthalate:isopentyl isononyl terephthalate: diisononyl terephthalate in the respective ester mixture).

All ranges below include the lowest and highest value of the range as well as all subvalues therebetween.

The present invention therefore provides a mixture comprising the terephthalic diesters I, II and III,

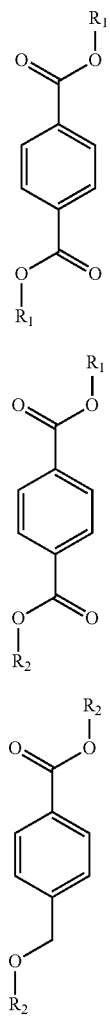

where $R_1$ is an alkyl radical having 5 carbon atoms and $R_2$ is an alkyl radical having 9 carbon atoms.

For the purposes of this specification, the terms "$R_1$", "alkyl radical having 5 carbon atoms", "pentyl radical" and "$C_5$ radical" are used synonymously. The same applies to the terms "$R_2$", "alkyl radical having 9 carbon atoms", "nonyl radical" and "$C_9$ radical". The prefix "iso" marks the fact that this is an isomer mixture with a common number of carbons. Where "an alcohol" is described below, for example "a $C_5$ alcohol" or "an alcohol having 5 carbon atoms", this alcohol may consist only of a single isomer or may comprise a mixture of two or more isomers; in other words, in the case of a $C_5$ alcohol, it may be an isopentanol.

Surprisingly it has been found that relative to known plasticizer compositions, mixtures according to the invention exhibit an improved interplay of the properties of volatility and gelling temperature. As can be seen from the plot in FIG. 2 of the gelling temperature against the volatility for mixtures according to the invention and for other plasticizer systems, mixtures according to the invention have lower gelling temperatures and at the same time lower volatilities in comparison to the other polymer-compatible, SVOC-free plasticizer systems, and therefore exhibit improved properties for processing and application relative to those plasticizer systems.

Preferably, in the formulae I, II and III, $R_1$ is 2-methylbutyl, 3-methylbutyl and/or n-pentyl radicals. More preferably $R_1$ in the formula I, II and III is isopentyl radicals, with the term isopentyl radicals, as defined above, describing a mixture of two or more isomeric pentyl radicals. $R_2$ in the formula I, II and III, is preferably nonyl or n-nonyl radicals. More preferably $R_2$ in the formulae I, II or III is isononyl radicals, with the term isononyl radicals, as defined above, describing a mixture of two or more isomeric nonyl radicals.

Preference is given to mixtures in which in the formulae I, II and III, $R_1$ is 2-methylbutyl, 3-methylbutyl, n-pentyl and/or isopentyl radicals and $R_2$ is isononyl radicals. Preference is given to mixtures in which in the formulae I, II and III, $R_2$ is nonyl, n-nonyl and/or isononyl radicals and $R_1$ is 2-methylbutyl radicals. Preference is given, moreover, to mixtures in which the formulae I, II and III, $R_2$ is nonyl, n-nonyl and/or isononyl radicals and $R_1$ is 3-methylbutyl radicals. Further preferred are mixtures in which in the formulae I, II and III, $R_2$ is nonyl, n-nonyl and/or isononyl radicals and $R_1$ is n-pentyl and/or isopentyl radicals.

Isononyl radicals present in the esters I, II and III of the mixture according to the invention preferably have an average degree of branching of 1.0 to 2.2, since within this range the compatibility of the mixtures according to the invention with polymers is increased. This average degree of branching is determined as described in the document US 2010/305255 A1.

In one embodiment, in the mixture according to the invention, the fraction of the n-pentyl radicals is at least 10 mol % or 20 mol %, preferably at least 30 mol %, more preferably at least 40 mol %, very preferably at least 50 mol % and more particularly at least 60 mol %, based on the entirety of the pentyl radicals present in the esters I, II and II, this being possibly linked with the advantage of a lower viscosity which is therefore more favorable for the processing of plastisols. In one preferred embodiment, the fraction of the n-pentyl radicals, based on all of the pentyl radicals present, is between 10 and 90 mol %, preferably 20 to 80 mol % and more particularly 30 to 70 mol %.

Particularly high compatibility of the polymer to be plasticized has been found for those mixtures according to the invention which comprise less than 80 mol %, preferably less than 70 mol % and more particularly less than 60 mol % of the ester III, based on the entirety of the esters I, II and III. In addition to the improved compatibility of these mixtures relative to mixtures which contain a higher fraction of ester III in the mixture of the esters I, II and III, mixtures with less than 80 mol %, preferably with less than 70 mol % and more particularly preferably with less than 60 mol % of ester III also have a lower gelling temperature, which is therefore more advantageous for the processing of plastisols, than mixtures which comprise a higher fraction of ester III.

A lower and hence improved volatility is exhibited by mixtures according to the invention which comprise less than 60 mol %, preferably less than 50 mol %, more preferably less than 40 mol %, very preferably less than 30 mol % and more particularly less than mol % of the ester I, based on the entirety of the esters I, II and II, and for this reason such mixtures are likewise preferred.

Mixtures according to the invention with a particularly favorable gelling temperature are present when the mixture comprises preferably less than 40 mol % and more particularly less than 30 mol % of the ester III, based on the entirety of the esters I, II and III. Mixtures of particularly low volatility comprise preferably more than 30 mol % and more particularly more than 40 mol % of the ester III, based on the entirety of the esters I, II and III.

In one embodiment of the present invention the mixture comprises at least 10 mol %, preferably at least 20 mol %, more preferably at least 30 mol % and more particularly at least mol % of the ester II and/or not more than 60 mol %, preferably not more than 50 mol %, more preferably not more than 40 mol % and more particularly not more than 30 mol % of the ester II, based in each case on the entirety of the esters I, II and III.

The mixtures according to the invention preferably comprise less than 40 wt %, more preferably less than 30 wt %, more preferably still less than 20 wt % and more particularly less than 10 wt % of components which do not fall within the definition of the esters I, II and III. More particularly, mixtures according to the invention preferably comprise less than mol %, more preferably less than 10 mol % and more particularly less than 3 mol % of terephthalic diesters which do not fall within the definition of the esters I, II and III, the determination of the molar fractions taking account of the entirety of all the terephthalic diesters in the mixture.

A preferred subject of the present invention is a mixture comprising the terephthalic diesters I, II and III,

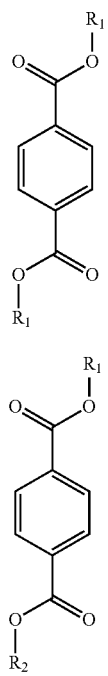

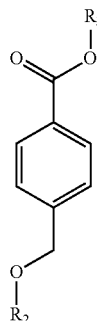

where $R_1$ is 2-methylbutyl, 3-methylbutyl, n-pentyl and/or isopentyl radicals and $R_2$ is isononyl radicals, which comprises less than 80 mol %, preferably less than 70 mol % and more particularly less than 60 mol % of the ester III, based on the entirety of the esters I, II and III.

A further subject of the present invention is the use of a mixture according to the invention as plasticizer for polymers. In this context the term "plasticizer"—as already elucidated above—should be understood to mean that the ester mixture of the invention on its own is the plasticizer, or the mixture according to the invention forms the plasticizer together with further polymer-plasticizing components.

Suitable polymers are preferably selected from the group consisting of polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atoms, acrylonitrile or cyclic olefins, polyvinylidene chloride (PVDC), polyacrylates, especially polymethyl methacrylate (PMMA), polyalkyl methacrylate (PAMA), polyureas, silylated polymers, fluoropolymers, especially polyvinylidene fluoride (PVDF), polytetrafluorethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphide (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

Preferred polymers are polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Particularly preferred is the use of an ester mixture of the invention as plasticizer for PVC.

The ester mixture is preferably used as plasticizer in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags.

A further subject of the present invention is a composition comprising an ester mixture of the invention and also one or more polymers from the group consisting of polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Based on 100 parts by mass of polymer, preferred compositions comprise from 5 to 200, preferably from 10 to 150, parts by mass of plasticizer.

Preferred is the use of the ester mixture of the invention as plasticizer for polyvinyl chloride, and particularly preferred, accordingly, are compositions which comprise the ester mixture of the invention and PVC.

The polymer is preferably a suspension-, bulk-, microsuspension- or emulsion-PVC.

Preferred compositions of the invention may comprise not only the ester mixture of the invention but also at least one further polymer-plasticizing compound, i.e. a further plasticizer. In one particularly preferred embodiment of the composition of the invention it comprises less than 5 mass % and more particularly less than 0.5 mass % of phthalate-containing compounds. The further plasticizers are preferably selected from the group of the adipates, benzoates, examples being monobenzoates or glycol dibenzoates, chlorinated hydrocarbons, citrates, cyclohexanedicarboxylates, epoxidized fatty acid esters, epoxidized vegetable oils, epoxidized acrylated glycerides, furandicarboxylates, phosphates, phthalates (preferably in very small amounts), succinates, sulphonamides, sulphonates, terephthalates, trimellitates or oligomeric or polymeric esters based on adipic, succinic or sebacic acid. Particularly preferred are alkyl benzoates, dialkyl adipates, glycerol esters, trialkyl citrates, acylated trialkyl citrates, trialkyl trimellitates, glycol dibenzoates, dialkyl terephthalates, esters of furandicarboxylic acid, dialkanoyl esters of dianhydrohexitols (e.g. isosorbitol) and dialkyl esters of 1,2-, 1,3- or 1,4-cyclohexanedicarboxylic acid.

In one embodiment the composition of the invention comprises not only the ester mixture of the invention but also less than 20 mass %, less than 10 mass % of, or, no further plasticizers, the mass % being based on the overall mass of the composition.

Compositions of the invention preferably comprise not only the polymer or a mixture of two or more polymers and the ester mixture of the invention but also one or more additives from the group of the heat stabilizers, fillers, pigments, blowing agents, biocides. UV stabilizers, light stabilizers, costabilizers, antioxidants, viscosity regulators, deaerating agents, adhesion promoters, lubricants and colorants.

The compositions of the invention can be used in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags.

Mixtures according to the invention can be prepared for example by esterification or transesterification processes.

Preparation Process I

In one embodiment of the present invention, mixtures according to the invention are prepared by esterification of terephthalic acid or a terephthalic acid derivative with an alcohol mixture of $C_5$ and $C_9$ alcohols.

A subject of the present invention is a process for preparing an ester mixture of the invention by esterifying terephthalic acid or a terephthalic acid derivative with a mixture comprising $R_1OH$ ($R_1$=alkyl radical having 5 carbon atoms) and $R_2OH$ ($R_2$=alkyl radical having 9 carbon atoms). A terephthalic acid derivative used with preference is dimethyl terephthalate (DMT).

Preparation Process II

In another embodiment of the present invention, the mixture according to the invention is prepared by reacting the ester I with less than 1 mole equivalent, based on the number of its ester functions, of alcohol which comprises 9 carbon atoms.

A subject of the present invention is a process for preparing an ester mixture of the invention wherein the ester I is reacted with less than 1 mole equivalent, based on the number of its ester functions, of an alcohol or of two or more alcohols having 9 carbon atoms (for short: $C_9$ alcohol) with accompanying heating, preferably to boiling (optionally in the presence of a catalyst).

The radicals $R_1$ and $R_2$ here are as defined earlier on above for the mixtures according to the invention. With particular preference $R_1$ is 2-methylbutyl, 3-methylbutyl, n-pentyl and/or isopentyl radicals and $R_2$ is isononyl radicals, the mixture preferably comprising less than 80 mol %, more preferably less than 70 mol % and more particularly less than 60 mol % of the ester III, based on the entirety of the esters I, II and III. Also valid are the preferred embodiments indicated earlier on above in relation to the isomer distributions of $R_1$ and $R_2$.

In this Preparation Process II, the ester I is reacted with less $C_9$ alcohol than would be necessary for the complete replacement of all the alcohol radicals of the ester functions within the ester I. Surprisingly it has been ascertained that the composition of the resulting ester mixture, comprising unmixed esters I and III and also the mixed ester II, can be adjusted in a targeted way—within the ambit of the statistics arising for the case of the complete incorporation of the alcohol radicals of the $C_9$ alcohol—when the ester I is introduced initially and the $C_9$ alcohol is added. Control of the ester mixture composition is not possible, in contrast, if an esterification or transesterification is carried out for which an alcohol mixture ($C_5$ alcohol+$C_9$ alcohol) of the alcohol radicals to be introduced is used or if $C_5$ alcohol is added to the ester III.

Hence it is possible by means of Preparation Process II to provide ester mixtures in which the different alcohol radicals are present in a predetermined quantitative distribution and in which, moreover, the quantitative distribution of the esters present can be controlled in a targeted way—within the statistics specified above. It is therefore possible to provide ester mixtures whose composition exhibits smaller deviations from the ester distribution arising from the statistics than ester mixtures prepared by uncontrolled processes described in the related art.

For the mixtures according to the invention that are prepared by means of Preparation Process II, the statistical expectation values arising are those set out in Table 1.

TABLE 1

Statistical expectation values (Preparation Process II)

| Input | | Expected amount | | |
|---|---|---|---|---|
| Ester I [$C_5$ equivalents] | $C_9$ alcohol [$C_9$ equivalents] | Ester I [mol %] | Ester II [mol %] | Ester III [mol %] |
| 2 | 0.2 | 81 | 18 | 1 |
| 2 | 0.4 | 64 | 32 | 4 |
| 2 | 0.6 | 49 | 42 | 9 |
| 2 | 0.8 | 36 | 48 | 16 |
| 2 | 1.0 | 25 | 50 | 25 |
| 2 | 1.2 | 16 | 48 | 36 |
| 2 | 1.4 | 9 | 42 | 49 |
| 2 | 1.6 | 4 | 32 | 64 |
| 2 | 1.8 | 1 | 18 | 81 |

The deviation of the ester mixture composition from the quantitative distribution, resulting from statistical considerations, of the esters in the ester mixture can be quantified by summing all of the amounts of the differences between the statistical expectation value which arises when complete incorporation of the alcohol radicals of the $C_9$ alcohol is assumed, and the actual molar fraction of each individual ester in the ester mixture in the event that the sum of the molar fractions of the abovementioned esters in the ester mixture adds up to 100.

By means of Preparation Process II it is possible, for example, to provide specifically, from 5.5 mol of diisopentyl terephthalate and 7.1 mol of isononanol, an ester mixture in which the molar distribution of the esters present deviates by only 4 points from the statistical expectation value, and the fraction of isopentyl radicals in the ester mixture corresponds to the intended isopentyl fraction to an accuracy of 1%.

In accordance with the invention, in Preparation Process II, less than 1 mole equivalent is used of $C_9$ alcohol, based on the number of ester functions present in the ester I (1 mole equivalent $C_5$ equivalent). The ester I is preferably reacted with less than 0.98 mole equivalent, preferably with less than 0.95 mole equivalent and more particularly with less than 0.90 mole equivalent, based on the number of its ester functions, of the $C_9$ alcohol. Preference may also be given to reacting the ester I with less than 0.85 mole equivalent, preferably with less than 0.80 mole equivalent and more particularly less than 0.75 mole equivalent of the $C_9$ alcohol, based on the number of its ester functions. Obtained in this way are ester mixtures which relative to the ester III have significantly more favorable, i.e. lower, gelling temperatures and which at the same time exhibit a lower and hence improved volatility relative to the ester I. Ester mixtures which can be processed particularly effectively with polymers, PVC for example, are obtained if the ester I is reacted with less than 0.85 mole equivalent, preferably with less than 0.80 mole equivalent and more particularly with less than 0.75 mole equivalent of $C_9$ alcohol, based on the number of its ester functions.

With preference the ester I is reacted with more than 0.05 mole equivalent, preferably with more than 0.10 mole equivalent and more particularly with more than 0.20 mole equivalent of the $C_9$ alcohol, based on the number of its ester functions. In many cases it is preferable for the ester I to be reacted with more than 0.25 mole equivalent, preferably with more than 0.30 mole equivalent and more particularly with more than 0.35 mole equivalent of the $C_9$ alcohol, based on the number of its ester functions. By these means it is possible to obtain ester mixtures which are suitable for producing ester mixture-containing and polymer-containing compositions having particularly good storage qualities. A further improvement in the properties in the area of volatility is possible if the ester I is reacted with more than 0.70 mole equivalent, preferably with more than 0.75 mole equivalent and more particularly with more than 0.80 mole equivalent of the $C_9$ alcohol, based on the number of its ester functions.

A preferred subject of the present invention is a process for preparing an ester mixture of the invention, comprising the esters dipentyl terephthalate, diisononyl terephthalate and pentyl isononyl terephthalate, in which dipentyl terephthalate is reacted with less than 1 mole equivalent, based on the number of its ester functions, of isononanol, with accompanying heating at boiling. In this case dipentyl terephthalate is reacted preferably with more than 0.05 mole equivalent but less than 0.98 mole equivalent, with less than 0.95 mole equivalent, with less than 0.90 mole equivalent, with less than 0.85 mole equivalent, with less than 0.80 mole equivalent, with less than 0.75 mole equivalent, with less than 0.70 mole equivalent or with less than 0.65 mole equivalent, based on the number of its ester functions, of the alcohol isononanol, with accompanying heating at boiling. Preferably here the pentyl radicals and the isononyl radicals have the isomer compositions elucidated earlier on above for the mixtures according to the invention.

In order to improve the controllability of the composition of the ester mixture resulting from the reaction of Preparation Process II, the reaction mixture during the reaction comprises preferably less than 0.5 mole equivalent, more preferably less than 0.1 mole equivalent, very preferably less than 0.05 mole equivalent and more particularly less than 00.1 mole equivalent of alcohols which are not $C_5$ alcohols and are not $C_9$ alcohols, the mole equivalents being based on the entirety of all of the alcohols present in the reaction mixture (corresponding to 1 mole equivalent).

The desired composition of the ester mixture to be prepared may be controlled to particularly good effect, and the process product utilized after a reduced work-up effort, directly as plasticizer or plasticizer component, if the components used in the process of the invention, comprising ester I and $C_9$ alcohol, comprise less than 50 vol %, preferably less than vol % and more particularly less than 20 vol %, more preferably less than 10 vol %, of components which are not reactants, end products or intermediates of the reaction of ester I with $C_9$ alcohol. More particularly, the components used in the process, comprising ester I and $C_9$ alcohol, ought to comprise preferably less than 15 wt %, more preferably less than 10 wt % and more particularly less than 5 wt % of terephthalic acid derivatives containing acid groups, in order not to jeopardize the controllability of the transesterification.

Solvents which can be used in Preparation Process 11 are, for example, toluene, xylene, benzene, cyclohexane or $C_5$ alcohol, preferably in amounts of up to at most 50 vol %, more preferably up to at most 35 vol % and more particularly up to at most 20 vol %, based in each case on the overall reaction mixture. The fraction of the solvents which are not $C_5$ alcohol, however, is preferably below 30 vol %, more preferably below 15 vol %, and more particularly below 1 vol %, based in each case on the overall reaction mixture.

In preferred embodiments, Preparation Process 11 allows the provision of mixtures according to the invention in which the molar ratio of the esters I, II and III deviates by less than 15 points, preferably by less than 10 points, from the statistically determined expectation value which is obtained if assuming complete incorporation of the $C_9$ alcohol radicals, this points value corresponding to the sum total of all amounts of the differences between statistical expectation value and actual molar fraction of each individual ester in the ester mixture in the event that the sum of the molar fractions of the aforementioned esters in the ester mixture adds up to 100.

Preparation Process II, and the Preparation Process III elucidated hereinafter, are carried out preferably in the presence of a catalyst or of two or more catalysts, for example using Brønsted or Lewis acids or bases as catalyst. Particularly suitable catalysts have been found to be sulphuric acid, methanesulphonic acid, p-toluenesulphonic acid, metals or their compounds. Examples of particularly preferred metal catalysts are tin powder, tin(II) oxide, tin(II) oxalate, titanic esters such as tetrairopropyl orthotitanate or tetrabutyl orthotitanate, and also zirconium esters such as tetrabutyl zirconate, and also sodium methoxide and potassium methoxide.

Preparation Process II can be carried out in typical esterification apparatus known to the skilled person, under customary process conditions. The process takes place preferably at temperatures at or above the boiling point of the $C_5$ alcohol, allowing the $C_5$ alcohol formed in the reaction to be removed from the reaction mixture by distillation under the prevailing pressure. In order to ensure quantitative recycling of $C_9$ alcohol located in the gas phase, the esterification apparatus ought preferably to be equipped with a column. The term "quantitative" refers in this context to an extent of more than 80 mol %, preferably more than 90 mol % and more particularly more than 95 mol %, based on the amount of the $C_9$ alcohol used.

In one particularly preferred embodiment of the process, more than 50 mol %, preferably more than 60 mol %, more preferably more than 70 mol %, very preferably more than 80 mol %, with preference more than 90 mol %, with particular preference more than 95 mol %, and more particularly more than 99 mol % of the $C_5$ alcohol which forms in the course of the process is removed from the reaction vessel during the process, preferably by distillation.

GC chromatograms are preferably prepared at regular intervals during the reaction, for observation of the progress of the reaction. With preference the reaction is terminated, by cooling and/or destruction of the catalyst, by addition of water and/or base, for example, when the GC chromatograms show a residual $C_9$ alcohol content of less than 5.0 area %, preferably of less than 2 area %, more preferably of less than 1.0 area % and more particularly of less than 0.5 area %, based on the total area of all the esters in the GC chromatogram.

It is particularly preferred for the catalyst to be destroyed when more than 60 mol %, preferably more than 70 mol %, more preferably more than 80 mol %, with preference more than 90 mol % and more particularly more than 95 mol % of the $C_5$ alcohol which forms in the course of the process has been removed from the reaction vessel. The destruction of the catalyst here takes place preferably after reaction monitoring has found reaction progress of at least 90%, for example by the finding, in the GC chromatograms monitoring reaction progress, of a residual CO alcohol content of less than 5.0 area %, preferably less than 2.0 area % and more particularly of less than 1.0 area %, based on the total area of all the esters in the GC chromatogram.

After the end of the reaction, the reaction mixture is worked up in a customary way.

A preferred subject of the present invention is a process for preparing an ester mixture according to the invention, comprising the esters I, II and III, wherein the ester I is reacted with less than 1 mole equivalent, based on the number of its ester functions, with an alcohol or with two or more alcohols having 9 carbon atoms, preferably in the presence of a catalyst, with accompanying heating at boiling, and more than 80 mol %, preferably more than 90 mol %, and more particularly more than 95 mol % of the $C_5$ alcohol which forms in the course of the process is removed from the reaction vessel during the process, preferably by distillation.

In this case, preferably, the molar ratio of the esters I, II and III deviates by less than points, preferably by less than 10 points from the statistically determined expectation value which arises when assuming complete incorporation of the $C_9$ alcohol radicals, this points value corresponding to the sum total of all amounts of the differences between statistical expectation value and actual molar fraction of each individual ester in the ester mixture in the event that the sum of the molar fractions of the abovementioned esters in the ester mixture adds up to 100.

Preparation Process III

In another embodiment of the present invention, the mixture according to the invention is prepared by reacting terephthalic acid or a terephthalic acid derivative with a mixture of $C_5$ and $C_9$ alcohols, the $C_5$ alcohol being used in excess, but the $C_9$ alcohol being used in an amount which corresponds to the amount of $C_9$ ester groups in the ester mixture according to the invention that is to be prepared.

A subject of the present invention is a process for preparing an ester mixture of the invention, comprising the terephthalic esters I, II and III, by reacting terephthalic acid or derivatives thereof which contain no ester groups COOR with a radical R whose alcohol ROH has a higher boiling point at a defined pressure than the alcohol $R_1OH$ of the radical $R_1OH$ at the same pressure, with an amount $(m_1+s_1)$ of $R_1OH$ and an amount $m_2$ of $R_2OH$ and the reaction mixture being heated at boiling, where $m_1$ und $m_2$ correspond to the mole equivalents of the alcohol radicals $OR_1$ ($C_5$ alcohol radical) and $OR_2$ ($C_9$ alcohol radical) to be introduced into terephthalic acid or derivatives thereof, and $s_1$ is greater than 0.

In Preparation Process III, the terephthalic acid derivative used is preferably dimethyl terephthalate (DMT).

As already described for the mixtures according to the invention, $R_1$ here is 2-methylbutyl, 3-methylbutyl and/or n-pentyl radicals. More preferably $R_1$ in the formulae I, II and III is isopentyl radicals, the term isopentyl radicals, as defined above, describing a mixture of two or more isomeric pentyl radicals. $R_2$ is preferably nonyl, n-nonyl radicals, or a mixture of two or more isomeric nonyl radicals, called isononyl radicals. In this case the pentyl radicals and the isononyl radicals preferably, furthermore, have the isomer compositions elucidated earlier on above for the mixtures according to the invention. More preferably $R_1$ is 2-methylbutyl, 3-methylbutyl, n-pentyl and/or isopentyl radicals and $R_2$ is isononyl radicals, the mixture comprising preferably less than 80 mol %, more preferably less than 70 mol % and more particularly less than 60 mol % of the ester III, based on the entirety of the esters I, II and III.

In one embodiment in this Preparation Process III, terephthalic acid is esterified to give the esters I, II and III.

In another embodiment in this Preparation Process III, a terephthalic diester is transesterified to give the esters I, II and III. In this case the alcohol ROH of the diester has a lower boiling point at a defined pressure than the $C_5$ alcohol(s) at the same pressure.

With preference, the alcohol radicals introduced in the course of Preparation Process III into terephthalic acid or derivatives thereof are part of an ester function to an extent of at least 95 mol %, preferably at least 98 mol %, more preferably at least 99 mol % and more particularly 100 mol %.

In Preparation Process III, terephthalic acid or a derivative thereof is reacted with a mixture of $C_5$ and $C_9$ alcohols. Surprisingly it has been found that the composition of the resultant ester mixture comprising the unmixed esters I and III and also the mixed ester II can be adjusted in a targeted way—in the context of the statistics which arise for the case of the complete incorporation of the $C_9$ alcohol radicals—when the $C_5$ alcohol is used in excess relative to the $C_5$ alcohol radicals to be inserted into terephthalic acid or derivatives thereof, but the amount of the $C_9$ alcohol used corresponds to the amount of the $C_9$ alcohol radicals to be inserted. Conversely, it is not possible to control the ester mixture composition if, in an esterification or transesterification, an excess of the mixture of the $C_5$ and $C_9$ alcohols is used in relation to the alcohol radicals to be inserted, or if terephthalic acid or a derivative thereof is reacted with a mixture of $C_5$ and $C_9$ alcohols, with the $C_9$ alcohol being used in excess relative to the $C_9$ alcohol radicals to be inserted into terephthalic acid or its derivatives.

Accordingly it is possible by means of Preparation Process III to provide ester mixtures in which the different alcohol radicals are contained in a predetermined quantitative distribution and in which, moreover, the quantitative distribution of the esters present can be controlled in a targeted way—within the bounds of the statistics mentioned above. It is possible, accordingly, to provide ester mixtures whose composition exhibits smaller deviations from the ester distribution arising from the basis of the statistics than for ester mixtures prepared by uncontrolled processes described in the related art.

For x=1, the statistical expectation values of the ester mixture composition are those set out in Table 1.

TABLE 2

Statistical expectation values (Preparation Process III)

| Input ratio $C_5OH$ to $C_9OH$ ($m_1:m_2$) | | Expected amount | | |
|---|---|---|---|---|
| $m_1$ | $m_2$ | Ester I [mol %] | Ester II [mol %] | Ester III [mol %] |
| 9 | 1 | 81 | 18 | 1 |
| 8 | 2 | 64 | 32 | 4 |
| 7 | 3 | 49 | 42 | 9 |
| 6 | 4 | 36 | 48 | 16 |
| 5 | 5 | 25 | 50 | 25 |
| 4 | 6 | 16 | 18 | 36 |
| 3 | 7 | 9 | 42 | 49 |
| 2 | 8 | 4 | 32 | 64 |
| 1 | 9 | 1 | 18 | 81 |

Quantifying the deviation of the ester mixture composition from the quantitative distribution of the esters in the ester mixture that results from statistical considerations is possible by summing of all of the amounts of the differences between the statistical expectation value, the value arising assuming complete incorporation of the $C_9$ alcohol radicals, and the actual molar fraction of each individual ester in the ester mixture in the event that the sum of the molar fractions of the aforementioned esters in the ester mixture adds up to 100.

The process of the invention allows the targeted provision, for example, from 5 mol of dimethyl terephthalate, 3.5 mol of isopentanol and 9 mol of isononanol, of an ester mixture in which the molar distribution of the esters present deviates by only 1 point from the statistical expectation value and in which the fraction of pentyl radicals in the ester mixture corresponds to as near as 0.3% to the intended pentyl fraction.

With preference, in Preparation Process III, the $C_5$- and $C_9$ alcohols are used at a ratio to one another such that the ratio of $m_1$ to $m_2$ ($m_1:m_2$) is in the range from 1:9 to 9:1, preferably in the range from 2:8 to 8:2, more preferably in the range from 3:7 to 7:3 and more particularly in the range from 4:6 to 6:4. If the $C_5$ and $C_9$ alcohols are used in an $m_1:m_2$ ratio of greater than 1.5:8.5, preferably greater than 2:8 and more particularly greater than 2.5:7.5, ester mixtures can be obtained which have much more favorable, i.e. lower, gelling temperatures relative to the ester III, and which at the same time, relative to the ester I, are distinguished by a lower and hence improved volatility. Ester mixtures which can be processed particularly effectively with polymers, for example PVC, can be obtained when the $C_5$ and $C_9$ alcohols are used in an $m_1:m_2$ ratio which is greater than 1.5:8.5, preferably greater than 2:8 and more particularly greater than 2.5:7.5. Ester mixtures which are suitable for producing compositions comprising ester mixture and comprising polymer and possessing good storage qualities can be obtained if the $C_5$ and $C_9$ alcohols are used in an $m_1:m_2$ ratio of less than 8:2, preferably less than 7.5:2.5 and more particularly less than 7:3. A further improvement in the properties in the area of volatility becomes possible when the $C_5$ and $C_9$ alcohols are used in an $m_1:m_2$ ratio of less than 4:6, preferably less than 3.5:6.5 and more particularly less than 3:7. In the formation of all these ratios, the "excess amount" $s_1$ of $C_5$ alcohol is disregarded.

The amount $s_1$ of $C_5$ alcohol which goes beyond the amount $m_1$ of the alcohol functions to be introduced into terephthalic acid or derivatives thereof may act as a solvent in Preparation Process III. If water is formed in the process, then the amount $s_1$ of $C_5$ alcohol acts preferably as an azeotrope former for the water, which can be distilled off as an azeotropic mixture with $C_5$ alcohol. The amount $s_1$ is preferably less than $m_1+m_2$, with particular preference less than $0.6 \cdot (m_1+m_2)$, preferably less than $0.5 \cdot (m_1+m_2)$, more preferably less than $0.4 \cdot (m_1+m_2)$, with further preference less than $0.3 \cdot (m_1+m_2)$ and more particularly less than $0.25 \cdot (m_1+m)$. If the amount $s_1$ is greater than $0.05 \cdot (m_1+m_2)$, preferably greater than $0.10 \cdot (m_1+m_2)$, more preferably greater than $0.15 \cdot (m_1+m_2)$ and more particularly greater than $0.20 \cdot (m_1+m_2)$, this represents a preferred embodiment of the Preparation Process III. The amount $s_1$ is preferably less than $(m_1+m_2)$, preferably less than $0.6 \cdot (m_1+m_2)$, more preferably less than $0.5 \cdot (m_1+m_2)$ and more particularly less than $0.4 \ (m_1+m_2)$ and at the same time preferably greater than $0.05 \cdot (m_1+m_2)$, more preferably greater than $0.10 \cdot (m+m_2)$ and more particularly greater than $0.15 \cdot (m_1+m_2)$.

A preferred subject of the present invention is a process for producing a mixture according to the invention, comprising dipentyl terephthalate, diisononyl terephthalate and pentyl(isononyl) terephthalate, by reacting terephthalic acid or derivatives thereof which contain no ester groups COOR having a radical R whose alcohol ROH has a higher boiling point at a defined pressure than pentanol at the same pressure, with an amount $(m_1+s_1)$ of pentanol and an amount $m_2$ of isononanol, the reaction mixture being heated at boiling and $m_1$ and $m_2$ corresponding to the molar equivalents of the alcohol radicals of pentanol and isononanol that are to be introduced into terephthalic acid or its derivatives, and $s_1$ being greater than 0 and being situated in particular in the range from 0.05 to 0.60 times $(m_1+m_2)$.

The pentyl radicals and the isononyl radicals here preferably have the isomer compositions elucidated earlier on above for the mixtures according to the invention.

The inventive process preferably does not use an excess amount of $C_9$ alcohol, but instead uses only the amount of $C_9$ alcohol which corresponds to the amount of $C_9$ alcohol radicals to be incorporated into the terephthalic acid or derivatives thereof, more particularly to the amount of $C_9$ alcohol radicals to be incorporated as part of ester functions in the terephthalic acid or derivatives thereof. "No excess amount" here means that preferably less than 0.2 mole equivalent, preferably less than 0.1 mole equivalent and more particularly of less than 0.05 mole equivalent, based on the number of the amount of $C_9$ alcohol used, is not incorporated into an ester function. Accordingly, preferably at least 0.8 mole equivalent, more preferably at least 0.9 mole equivalent and more particularly 0.95 mole equivalent of the $C_9$ alcohol used in the process of the invention is introduced as $C_9$ alcohol radical into terephthalic acid or derivative thereof.

The desired composition of the ester mixture to be produced can be controlled particularly effectively, and the process product, after a lower work-up effort, can be utilized directly as plasticizer or plasticizer component, if the components used in the process of the invention, comprising terephthalic acid or derivatives thereof and the $C_5$ and $C_9$ alcohol mixture, contain less than 50 vol %, preferably less than 35 vol % and more particularly less than 20 vol %, with further preference less than 10 vol %, of components which are not reactants, end products or intermediates in the reaction of terephthalic acid or derivatives thereof with $C_5$ and $C_9$ alcohols. These quantity figures do not include the amount $s_1$ of $C_5$-alcohol. This amount, however, does include any alcohol which is not a $C_5$ or $C_9$ alcohol. In order to improve the controllability of the composition of the ester mixture resulting from the reaction of Preparation Process II, the reaction mixture during the reaction comprises preferably less than 0.5 mole equivalent, more preferably less than 0.1 mole equivalent, very preferably less than 0.05 mole equivalent and more particularly less than 0.01 mole equivalent of alcohols which are not $C_5$ alcohols and are not $C_9$ alcohols, the molar equivalents being based on the entirety of all of the alcohols present in the reaction mixture (corresponding to 1 mole equivalent).

In preferred embodiments, Preparation Process III enables the provision of mixtures according to the invention wherein the molar ratio of the esters I, II and III is different by less than 15 points, preferably by less than 10 points, from the statistically determined expectation value which arises when complete incorporation of the $C_9$ alcohol radical, this points value corresponding to the sum total of all amounts of the differences between statistical expectation value and actual molar fraction of each individual ester in the ester mixture in the event that the sum of the molar fractions of the aforementioned esters in the ester mixture adds up to 100.

Preparation Process III can be carried out in typical esterification apparatus, known to the skilled person, under customary process conditions. The process takes place preferably at temperatures at or above the boiling point of the $C_5$ alcohol, of the boiling point of water and/or of the boiling point of an azeotropic formed from $C_5$ alcohol and water, and so the excess amount $s_1$ of the $C_5$ alcohol can be distilled off from the reaction mixture at the prevailing pressure. Further improvement in the controllability of the composition of the ester mixture resulting from Preparation Process III is achieved if the process is carried out in an apparatus with column. This ensures preferably that $C_9$ alcohol present in the gas phase during the reaction is returned as far as possible quantitatively into the reaction vessel. The term "quantitatively" in this context means to an extent of more than 80 mol %, preferably more than 90 mol % and more particularly more than 95 mol %.

The water formed in the reaction is preferably removed from the reaction space. Here, preferably, the $C_5$ alcohol serves as azeotrope former. In the process of the invention there may optionally be further azeotropic former, for example cyclohexane, toluene, benzene or xylene, used.

The time needed to implement the process of the invention can be shortened if the two alcohols $R_1OH$ and $R_2OH$ are not used concurrently; instead, at least parts of the alcohol $R_1OH$ are added later than the alcohol $R_2OH$ to the terephthalic acid or derivatives thereof. Preferably, therefore, at least parts of the alcohol $R_1OH$ are reacted later than the alcohol $R_2OH$ with terephthalic acid or its derivatives. With preference, terephthalic acid (or its derivatives) is heated at boiling with the alcohol $R_2OH$ and optionally with a catalyst and also with parts of $R_1OH$, and the remaining parts of the alcohol $R_1OH$ are added to this reaction mixture only at a later point in time.

During the reaction, preferably, GC chromatograms are prepared, or the acid number is determined, at regular intervals, in order to observe the progress of the reaction. With preference the reaction is discontinued by cooling and/or destruction of the catalyst, by addition of water and/or base, for example, when the residual amount of terephthalic acid used or of the respective acid derivative used falls below a defined level in the GC chromatograms. If terephthalic acid is used in the process of the invention, then the reaction is discontinued preferably after the acid number of the reaction mixture falls below a level of 1.00 mg of KOH, more particularly a level of 0.50 mg of KOH, per g of reaction mixture. The acid number can be determined according to DIN EN ISO 2114. If a terephthalic acid derivative, for example a dimethyl terephthalate, is used in the process of the invention, it is possible to define, as a limiting point of a reaction which has proceeded substantially to completion, the amount of the component used itself or else the amount of an intermediate—for example, in the case where dimethyl ester is used, the amount of all monomethyl esters within the reaction mixture, this determination taking place preferably by means of GC. With preference the reaction is discontinued, by cooling and/or destruction of the catalyst, when a residual amount of terephthalic acid used or of terephthalic acid derivative used, or of an intermediate, such as monomethyl ester, for example, of less than 5.0 area %, preferably of less than 2.0 area % and more particularly of less than 1.0 area %, based on the total area of all the esters in the GC chromatogram, is found in the GC chromatograms.

In one particularly preferred embodiment of the Preparation Process III, a catalyst is used and is destroyed when the amount of $C_5$ alcohol in the reaction mixture has fallen to less than 15 vol %, preferably to less than 10 vol % and more particularly to less than 5 vol %, based on the volume of the overall reaction mixture. With particular preference the amount of $C_5$ alcohol in this case is lowered to less than 3 vol % and more particularly to less than 1 vol %, based on the volume of the entire reaction mixture, preferably by distillative removal. In one particularly preferred embodiment of the process of the invention, a catalyst is used in the process and the amount of $C_5$ alcohol in the reaction mixture is lowered to less than mol %, preferably to less than 15 mol %, more preferably to less than 10 mol %, and more particularly to less than 5 mol %, based on the excess amount $s_1$ of the $C_5$ alcohol, before the catalyst is destroyed. In this case the destruction of the catalyst takes place preferably when reaction monitoring shows reaction progress of at least 90% for example by the finding, in the GC chromatograms used to monitor reaction progress, of a residual amount of terephthalic acid used or of acid derivative used, or of intermediate, such as monomethyl ester, for example, of less than 5.0 area %, more particularly of less than 1.0 area %, based on the total area of all the esters in the GC chromatogram, or by the acid number falling below a defined level. By lowering the amount of C alcohol, the process of the invention to form ester mixtures whose compositions have particularly small deviations from the statistical expectation value can be controlled more effectively.

A preferred subject of the present invention is a process for preparing an ester mixture of the invention by reaction of terephthalic acid or derivatives thereof which contain no ester groups COOR having a radical R whose alcohol ROH has a higher boiling point at a defined pressure than the alcohol $R_1OH$ of the radical $R_1$ at the same pressure, with an amount $(m_1+s_1)$ of $R_1OH$ and an amount $m_2$ $R_2OH$, in which the reaction mixture is heated at boiling, the reaction is discontinued preferably after reaction progress of at least 90% has been found, for example by the acid number of the reaction mixture falling below a level of 1.00 mg of KOH per g of reaction mixture, more particularly a level of 0.50 mg of KOH per g of reaction mixture, or by the determination in the GC chromatograms of a residual amount of a component used during the reaction, or of an intermediate formed and consumed during the reaction, of less than 5.0 area %, more particularly of less than 1.0 area %, based on the total area of all the esters in the GC chromatogram, preferably at least 0.8 mole equivalent, more preferably at least 0.9 mole equivalent and particularly at least 0.95 mole equivalent of the alcohol $R_2OH$ used in the process of the invention is introduced as $OR_2$ radical into the terephthalic acid or derivative thereof, a catalyst is used and in the reaction mixture the amount of $R_1OH$ was lowered to less than 20 mol %, preferably to less than 15 mol %, more preferably to less than 10 mol % and more particularly to less than 5 mol %, based on the excess amount $s_1$ of the alcohol $R_1OH$, before the catalyst is destroyed, and where $m_1$ and $m_2$ correspond to the mole equivalents of the $OR_1$ and $OR_2$ alcohol radicals to be introduced into the terephthalic acid or derivatives thereof, and $s_1$ is greater than 0 and more particularly is situated in the range from 0.01 to 0.60 times $(m_1+m_2)$.

$R_2$ here is preferably isononyl and with preference, moreover, the molar ratio of the esters I, II and III is different by less than 15 points, preferably by less than 10 points, from the statistically determined expectation value which arises when complete incorporation of the isononyl alcohol radical is assumed, this points value corresponding to the sum total of all amounts of the differences between statistical expectation value and actual molar fraction of each individual ester in the ester mixture in the event that the sum of the molar fractions of the aforementioned esters in the ester mixture adds up to 100.

A further subject of the invention is the use of Preparation Process II and III for setting processing-relevant and/or application-relevant properties of an ester mixture by control of the quantitative distribution of the esters in the ester mixture. Examples of the influencing of certain processing-relevant and application-relevant properties in the area of plasticizers through the choice of the amounts of $C_9$ alcohol used in Preparation Process II and/or through the choice of the $m_1:m_2$ ratio in Preparation Process III have been given above in the text.

A particularly preferred subject of the present invention is the use of Preparation Process II and III for controlling the gelling temperature of a plastisol containing terephthalic acid ester mixture and/or for controlling the volatility of a test specimen containing terephthalic acid ester mixture, by control of the quantitative distribution of the esters in the ester mixture. FIG. 1, for ester mixtures of the invention with different quantitative distributions of the esters present, plots the gelling temperature of the plastisols against the associated volatility of the films comprising the same ester mixture. From this figure it is apparent that products (plastisols or films) of different mixtures according to the invention have volatilities and gelling temperatures which deviate from one another, and the skilled person is able to select the appropriate ester mixture composition in accordance with the volatility and gelling temperature that are needed for processing and/or application. The same is true of other properties, such as, for example, the compatibility of the ester mixtures with polymers, as may be determined by methods including the test that is described in the experimental section; the Shore hardness, which describes plasticizer efficiency; the change in the viscosity of a corresponding plastisol after storage; or the change in mass of a corresponding plastisol on water storage. The process of the invention therefore allows the skilled person to produce ester mixtures having the desired properties in a targeted way, since the quantitative distribution of the esters in the ester mixture can be adjusted in a targeted way by means of the process of the invention.

Having generally described this invention, a further understanding can be obtained by reference to certain specific examples which are provided herein for purposes of illustration only, and are not intended to be limiting unless otherwise specified.

Experimental Section:

Boiling Range of the Alcohols:

The alcohols used in the examples or for synthesis of the esters used in the examples have the following boiling ranges:

Isononanol (Evonik Industries AG, purity >99%): 205 to 215° C. at 1013 hPa;

Isopentanol (mixture of n-pentanoi (Sigma Aldrich, purity >99%) and 2-methylbutanol (Sigma Aldrich, purity >99%) in a 1:1 molar ratio): 129 to 138° C. at 1013 hPa Acid Number:

The acid number was determined in accordance with DIN EN ISO 2114.

Gc Analyses:

The GC analysis took place with the following parameters:

Capillary column: 30 m DB5; 0.25 mm ID; 0.25 µm film

Carrier gas: Helium

Column pressure: 80 kPa

Split: about 23.8 ml/min

Oven temperature program (duration: 51 min): 50° C. (for 1 min), heating at 7.5° C./min to 350° C. (hold temperature for 1 min)

Injector: 350° C.

Detector (FID): 400° C.

Injection volume: 1.0 µl

Components in the sample chromatogram were identified using a comparative solution of the relevant esters. This was followed by standardization of the signals in the sample chromatogram to 100 area %. The ratios of the amounts of substance were determined in sufficient approximation from the area ratios of the individual signals.

The purity was determined via the fraction of the product signals as a proportion of the total areas in the chromatogram.

Example 1 (Inventive)

Transesterification of Dimethyl Terephthalate with Isopentanol and Isononanol by Preparation Process III (13:46:41)

A transesterification apparatus comprising a stirred flask with stirrer, dip tube, thermometer and 20 cm Raschig ring column with top-mounted distillation head was charged with dimethyl terephthalate (Sigma Aldrich, purity >99%) ($m_b$) and the alcohols $R_1OH$ ($m_1+s_1$) and $R_2OH$ ($m_2$). The apparatus was flushed with nitrogen (6 l/h) by the dip tube for at least one hour. Then 0.25 wt % of tetra-n-butyltitanate (Sigma Aldrich, purity >97%), based on the mass of the terephthalic ester, was added. The mixture was subsequently heated at boiling and low-boiling components were distilled off. When there was a sharp increase in the overhead temperature, the distillation was interrupted by closing the drain tap and the reaction was left at reflux until a stable boiling temperature was established. During the reaction, the liquid phase temperature rose from $T^1$ to $T^2$. During the reaction, GC chromatograms were prepared hourly. As soon as these chromatograms showed a residual monomethyl ester content of less than 0.5 area %, based on the total area of all the esters in the GC chromatogram, the remaining volatile components in the reaction mixture were distilled off under reduced pressure (about 1 mbar) at a liquid phase temperature of $T^3$, making the residual alcohol $R_1OH$ content less than 5 mol %, based on the excess amount $s_1$ of the alcohol $R_1OH$ (according to GC). The contents of the flask were then cooled to about 80° C. with the heating shut off by introduction of nitrogen at 20 mbar. The acid number of the flask contents was determined. Corresponding to the result, the reaction medium was neutralized by slow dropwise addition of three times the stochiometric amount of base (10% strength aqueous NaOH solution) and stirred at 80° C. for 15 minutes with introduction of nitrogen (6 l/h). The batch was then slowly evacuated from the ambient pressure to about 1 mbar, at which point it was heated to about 120° C. and remaining volatile constituents were separated off by means of nitrogen introduction at constant temperature. The stream of nitrogen is set such that the pressure did not exceed 20 mbar. As soon as GC analysis indicated the residual alcohol content to be less than 0.025 area %, the heating was shut off and cooling took place to 80° C. under reduced pressure and with introduction of nitrogen. At this temperature, the product was filtered through a Büchner funnel with filter paper and pre-pressed filter-aid filter cake (Perlite type D14) into a suction flask by means of reduced pressure. A GC analysis was carried out on the filtrate, to determine the purity (R) and the composition of the product.

TABLE 3 measured and calculated values for Example 1 (Preparation Process III)

| | |
|---|---|
| $R_1OH$ = isopentanol | $m_1 + s_1$ = 441 g |
| Amount of $R_1OH$ = | 5 mol |
| Amount of $R_1$ equivalents ($C_5$) | |
| $R_2OH$ = isononanol | $m_2$ = 720 g |
| Amount of $R_2OH$ = | 5 mol |
| Amount of $R_2$ equivalents ($C_9$) | |
| Dimethyl terephthalate | $m_b$ = 776 g |
| Amount | 4 mol |
| → Amount of ester functions | 8 mol |
| Expected molar fraction of the RI functions as a proportion of $R_1$ and $R_2$ functions in the ester mixture (on complete incorporation of $R_2$) | 8 mol − 5 mol = 3 mol corresponding to 37.5 mol % |
| Ratio $m_1$:$m_2$ | 3:5 corresponding to 0.375:0.625 |
| $s_1$ | 5 mol − (8 mol − 5 mol) = 2 mol |
| $T^1 \to T^2$ (liquid phase temperature start → end) | 139° C. → 215° C. |
| $T^3$ | 190° C. |
| R (purity) | 99.7% |
| Statistical expectation values for complete incorporation of $C_9$: | |
| ($C_5/C_5$):($C_5/C_9$):($C_9/C_9$) | 14.1:46.8:39.1 (expected $C_5$ fraction: 37.5%) |
| Composition by GC ($C_5/C_5$):($C_5/C_9$):($C_9/C_9$) | 13.4:45.8:40.8 ($C_5$ fraction: 36%) Deviation: \|14.1 − 13.4\| + \|46.8 − 45.8\| + \|39.1 − 40.8\| = 3.4 |

1270 g of worked-up ester mixture are obtained 13:46:41 ($C_5/C_9$ TM 13:46:41).

Example 2 (Inventive)

Transesterification of Dimethyl Terephthalate with Isopentanol and Isononanol by Preparation Process II (1:19:81)

Example 2 is carried out as described for Example 1.

TABLE 4 measured and calculated values for Example 2 (Preparation Process III)

| | |
|---|---|
| $R_1OH$ = isopentanol | $m_1 + s_1$ = 308.5 g |
| Amount of $R_1OH$ = | 3.5 mol |
| Amount of $R_1$ equivalents ($C_5$) | |
| $R_2OH$ = isononanol | $m_2$ = 1296 g |
| Amount of $R_2OH$ = | 9 mol |
| Amount of $R_2$ equivalents ($C_9$) | |
| Dimethyl terephthalate | $m_b$ = 970 g |
| Amount | 5 mol |
| → Amount of ester functions | 10 mol |
| Expected molar fraction of $R_1$ functions as a proportion of $R_1$ and $R_2$ functions in the ester mixture (on complete incorporation of $R_2$) | 10 mol − 9 mol = 1 mol corresponding to 10 mol % |
| Ratio $m_1$:$m_2$ | 0.1:0.9 |
| $s_1$ | 3.5 mol − (10 mol − 9 mol) = 2.5 mol |
| $T^1 \to T^2$ (liquid phase temperature start → end) | 131° C. → 200° C. |
| $T^3$ | 200° C. |
| R (purity) | >99.9% |
| Statistical expectation values for complete incorporation of $C_9$: | |
| ($C_5/C_5$):($C_5/C_9$):($C_9/C_9$) | 1.0:18.0:81.0 (expected $C_5$ fraction: 10%) |

TABLE 4-continued measured and calculated values for Example 2 (Preparation Process III)

| | |
|---|---|
| Composition by GC $(C_5/C_5):(C_5/C_9):(C_9/C_9)$ | 1.0:18.5:80.5 ($C_5$ fraction: 10.3%) Deviation: $\|1 - 1\| + \|18.5 - 18.0\| + \|80.5 - 81.0\| = 1$ |

1902 g of worked-up ester mixture are obtained—1:19:81.

Example 3 (Inventive)

Transesterification of Diisopentyl Terephthalate with Isononanol by Preparation Process II (11:45:44)

Example 3 was carried out as described for Example 1, but replacing the reactants isopentanol, isononanol and dimethyl terephthalate used by diisopentyl terephthalate (ester I in an amount $m_E$) and isononanol (in the amount $m_{R2}$) with the stated catalyst (in the catalyst amount stated). The reaction was terminated by cooling as soon as the hourly GC chromatograms recorded showed a residual isononanol content of less than 0.5 area %, based on the total area of all the terephthalic esters, and the remaining volatile components were distilled off under reduced pressure (about 1 mbar) to an extent such that the residual isopentanol content was below 5 mol %, based on the total amount of the isopentanol formed in the reaction (calculated via area % in the GC, based on terephthalic esters containing isononyl alcohol radical).

TABLE 5 measured and calculated values for Example 3 (Preparation Process II)

| | |
|---|---|
| $m_E$ (diisopentyl terephthalate) Amount of $R_1$ equivalents ($C_5$) | 1697 g (5.5 mol) 11 mol |
| $m_{R2}$ (isononanol) Amount of $R_2OH$ = Amount of $R_2$ equivalent ($C_9$) | 1025 g 7.1 mol |
| Quantitative ratio used $R_1$ equivalents to $R_2$ equivalents ($C_5$:$C_9$) | 11.0:7.1 corresponding to 2.0:1.3 |
| $T^1 \rightarrow T^2$ (liquid phase temperature start $\rightarrow$ end) | 170° C. $\rightarrow$ 202° C. |
| R (purity) | >99.9% |
| Statistical expectation values for complete incorporation of $C_9$: | |
| $(C_5/C_5):(C_5/C_9):(C_9/C_9)$ | 12:46:42 (expected $C_5$ fraction: 35%) |
| Composition by GC $(C_5/C_5):(C_5/C_9):(C_9/C_9)$ | 11:45:44 ($C_5$ fraction: 34%) Deviation: $\|12 - 11\| + \|46 - 45\| + \|42 - 44\| = 4$ |
| $R_1OH$ = isopentanol Amount of $R_1OH$ = Amount of $R_1$ equivalents ($C_5$) | $m_1 + s_1$ = 436 g 4.95 mol |
| $R_2OH$ = isononanol Amount of $R_2OH$ = Amount of $R_2$ equivalents ($C_9$) | $m_2$ = 7.2 g 0.05 mol |
| Dimethyl terephthalate Amount $\rightarrow$ Amount of ester functions | $m_b$ = 388 g 2 mol 4 mol |
| Expected molar fraction of $R_1$ functions as a proportion of $R_1$ and $R_2$ functions in ester mixture (on complete incorporation of $R_2$) | 4 mol – 0.05 mol = 3.95 mol corresponding to 10 mol % |
| Ratio $m_1$:$m_2$ | 3.95:0.05 corresponding to 0.988:0.012 |
| $s_1$ | 4.95 mol – (4 mol – 0.05 mol) = 1 mol |

TABLE 5-continued measured and calculated values for Example 3 (Preparation Process II)

| | |
|---|---|
| $T^1 \rightarrow T^2$ (liquid phase temperature start $\rightarrow$ end) | 124° C. $\rightarrow$ 195° C. |
| $T^3$ | 190° C. |
| R (purity) | 99.7% |
| Statistical expectation values for complete incorporation of $C_9$: | |
| $(C_5/C_5):(C_5/C_9):(C_9/C_9)$ | 97.6:2.4:<0.1 (expected $C_5$-fraction: 98.7%) |
| Composition by GC $(C_5/C_5):(C_5/C_9):(C_9/C_9)$ | 97:3:0 ($C_5$ fraction: 98.5%) Deviation: $\|97.6 - 97\| + \|2.4 - 3.0\| = 1.2$ |

652 g of worked-up ester mixture are obtained—97:3:0.

Example 5 (Inventive)

Transesterification of Dimethyl Terephthalate with Isopentanol and Isononanol by Preparation Process III (24:51:25)

Example 5 is carried out as described for Example 1.

TABLE 7 measured and calculated values for Example 5 (Preparation Process III)

| | |
|---|---|
| $R_1OH$ = isopentanol Amount of $R_1OH$ = Amount of $R_1$ equivalents ($C_5$) | $m_1 + s_1$ = 705 g 8 mol |
| $R_2OH$ = isononanol Amount of $R_2OH$ = Amount of $R_2$ equivalents ($C_9$) | $m_2$ = 576 g 4 mol |
| Dimethyl terephthalate Amount $\rightarrow$ Amount of ester functions | $m_b$ = 776 g 4 mol 8 mol |
| Expected molar fraction of $R_1$ functions as a proportion of $R_1$ and $R_2$ functions in the ester mixture (on complete incorporation of $R_2$) | 8 mol – 4 mol = 4 mol corresponding to 50 mol % |
| Ratio $m_1$:$m_2$ | 0.5:0.5 |
| $s_1$ | 8 mol – (8 mol – 4 mol) = 4 mol |
| $T^1 \rightarrow T^2$ (liquid phase temperature start $\rightarrow$ end) | 123° C. $\rightarrow$ 174° C. |
| $T^3$ | 180° C. |
| R (purity) | 99.9% |
| Statistical expectation values for complete incorporation of $C_9$: | |
| $(C_5/C_5):(C_5/C_9):(C_9/C_9)$ | 25:50:25 (expected $C_5$ fraction: 50%) |
| Composition by GC $(C_5/C_5):(C_5/C_9):(C_9/C_9)$ | 24:51:25 ($C_5$ fraction: 49.5%) Deviation: $\|25 - 24\| + \|51 - 50\| + \|25 - 25\| = 2$ |

1254 g of worked-up ester mixture are obtained—24:51:25 ($C_5/C_9$ TM 24:51:25).

Example 6 (Inventive)

Transesterification of Dimethyl Terephthalate with Isopentanol and Isononanol by Preparation Process III (44:45:11)

Example 6 is carried out as described for Example 1

TABLE 8

| measured and calculated values for Example 6 (Preparation Process III) | |
|---|---|
| $R_1OH$ = isopentanol Amount of $R_1OH$ = | $m_1 + s_1$ = 846 g 9.6 mol |
| Amount of $R_1$ equivalents ($C_5$) | |
| $R_2OH$ = isononanol Amount of $R_2OH$ = | $m_2$ = 346 g 2.4 mol |
| Amount of $R_2$ equivalents ($C_9$) | |
| Dimethyl terephthalate Amount → Amount of ester functions | $m_b$ = 776 g 4 mol 8 mol |
| Expected molar fraction of $R_1$ functions as a proportion of $R_1$ and $R_2$ functions in the ester mixture (on complete incorporation of $R_2$) | 8 mol − 2.4 mol = 5.6 mol corresponding to 70 mol % |
| Ratio $m_1:m_2$ | 5.6:2.4 corresponding to 0.7:0.3 |
| $s_1$ | 9.6 mol − (8 mol − 2.4 mol) = 4 mol |
| $T^1 \to T^2$ (liquid phase temperature start→ end) | 123° C. → 166° C. |
| $T^3$ | 190° C. |
| R (purity) | 99.8% |
| Statistical expectation values for complete incorporation of $C_9$: | |
| $(C_5/C_5):(C_5/C_9):(C_9/C_9)$ | 49:42:9 (expected $C_5$ fraction: 70%) |
| Composition by GC $(C_5/C_5):(C_5/C_9):(C_9/C_9)$ | 44:45:11 ($C_5$ fraction: 66.5%) Deviation: \|49 − 44\| + \|45 − 42\| + \|11 − 9\| = 10 |

1174 g of worked-up ester mixture are obtained—44:45:11 ($C_5/C_9$ TM 44:45:11).

Example 7 (Inventive)

Transesterification of Dimethyl Terephthalate with Pentanol and Isononanol (3:27:70)

Example 7 is carried out as described for Example 1. An ester mixture is obtained having a composition $(C_5/C_5):(C_5/C_9):(C_9/C_9)$ of 3:27:70 ($C_5/C_9$ TM 3:27:70) by GC.

Contrasting of Processing-Relevant and Application-Relevant Properties of Inventive Mixtures and Non-Inventive Mixtures The following mixtures comprising terephthalic esters of the formulae I, II and III with the definition of the radicals $R_1$ and $R_2$ as indicated in Table 9 were investigated.

The mixtures comprising the mixed ester (abbreviated hereinafter to "TM") were prepared as elucidated in Example 1, but with the corresponding alcohols. Alcohols used were as follows:

Ethylhexanol: 2-ethylhexanol from Sigma Aldrich, purity >99%

Butanol: n-butanol from Sigma Aldrich, purity >99%

Propylheptanol: 2-propylheptanol from Evonik Industries, C10 alcohols content >99%

Tridecanol: Marlipal O13 isotridecanol from Sasol, purity >99% C13 alcohols

The mixed ester-free mixtures (abbreviated below to "blend") were prepared by blending the respective terephthalates. Terephthalates used were as follows:

DINT: prepared by transesterifying dimethyl terephthalate (Sigma Aldrich, purity >99%) with isononanol (as indicated at the start of the Experimental Section);

DPT: prepared by transesterifying dimethyl terephthalate (Sigma Aldrich, purity >99%) with isopentanol (as indicated at the start of the Experimental Section);

DEHT: Eastman 168, Eastman, ester content >99%;

Dibutyl terephthalate: Di(n-butyl) terephthalate, Eastman DBT, Eastman, ester content >99%.

TABLE 9 terephthalic ester mixtures investigated (referred to below as "respective plasticizer from Table 9")

| $R_1$ | $R_2$ | Molar ratio of the esters I:II:III | | Designation |
|---|---|---|---|---|
| Ethylhexyl | Ethylhexyl | | | DEHT |
| Isononyl | Isononyl | | | DINT |
| Isopentyl | Isopentyl | | | DPT |
| Butyl | Ethylhexyl | 3:27:70 | Prepared in analogy to Example 1 | $C_4/C_8$ TM 3:27:70 |
| Butyl | Ethylhexyl | 11:45:24 | II | $C_4/C_8$ TM 11:45:24 |
| Butyl | Ethylhexyl | 26:50:24 | II | $C_4/C_8$ TM 26:50:24 |
| Isopentyl | Isononyl | 3:27:70 | Example 7 | $C_5/C_9$ TM 3:27:70* |
| Isopentyl | Isononyl | 13:46:41 | Example 1 | $C_5/C_9$ TM 13:46:41* |
| Isopentyl | Isononyl | 24:51:25 | Example 5 | $C_5/C_9$ TM 24:51:25* |
| Isopentyl | Isononyl | 44:45:11 | Example 6 | $C_5/C_9$ TM 44:45:11* |
| Isopentyl | Propylheptyl | 53:40:7 | Prepared in analogy to Example 1 | $C_5/C_{10}$ TM 53:40:7 |
| Isopentyl | Propylheptyl | 36:49:15 | II | $C_5/C_{10}$ TM 36:49:15 |
| Isopentyl | Propylheptyl | 18:50:32 | II | $C_5/C_{10}$ TM 18:50:32 |
| Isopentyl | Tridecyl | 49:44:7 | II | $C_5/C_{13}$ TM 49:44:7 |
| Isopentyl | Tridecyl | 29:52:19 | II | $C_5/C_{13}$ TM 29:52:19 |
| Isopentyl | Tridecyl | 13:51:36 | II | $C_5/C_{13}$ TM 13:51:36 |
| Ethylhexyl | Isononyl | 7:38:55 | II | $C_8/C_9$ TM 7:38:55 |
| Ethylhexyl | Isononyl | 20:46:34 | II | $C_8/C_9$ TM 20:46:34 |
| Ethylhexyl | Isononyl | 38:48:14 | II | $C_8/C_9$ TM 38:48:14 |
| Ethylhexyl | Propylheptyl | 7:38:55 | II | $C_8/C_{10}$ TM 7:38:55 |
| Ethylhexyl | Propylheptyl | 17:49:34 | II | $C_8/C_{10}$ TM 17:49:34 |
| Ethylhexyl | Propylheptyl | 35:48:17 | II | $C_8/C_{10}$ TM 35:48:17 |
| Butyl | Isononyl | 10:0:90 | Mixture of DINT and dibutyl terephthalate | $C_4/C_9$ Blend 10:90 |
| Butyl | Isononyl | 20:0:80 | II | $C_4/C_9$ Blend 20:80 |
| Butyl | Isononyl | 40:0:60 | II | $C_4/C_9$ Blend 40:60 |
| Butyl | Isononyl | 60:0:40 | II | $C_4/C_9$ Blend 60:40 |
| Butyl | Isononyl | 80:0:20 | II | $C_4/C_9$ Blend 80:20 |
| Isopentyl | Isononyl | 80:0:20 | Mixture of DINT and DPT | $C_5/C_9$ Blend 80:20 |
| Isopentyl | Isononyl | 60:0:40 | II | $C_5/C_9$ Blend 60:40 |
| Isopentyl | Isononyl | 40:0:60 | II | $C_5/C_9$ Blend 40:60 |
| Isopentyl | Isononyl | 20:0:80 | II | $C_5/C_9$ Blend 20:80 |

*inventive

Example 8

Preparation of Plastisols of the Mixtures

PVC plastisols were produced, as used, for example, for the manufacture of topcoat films for floor coverings. The figures in the plastisol formulations are each in parts by mass. The formulations of the polymer compositions are listed in Table 10.

TABLE 10

Plastisol formulation

| | |
|---|---|
| PVC (Vestolit B 7021 - Ultra; from Vestolit) | 100 |
| Respective plasticizer from Table 9 | 50 |
| Epoxidized soybean oil as costabilizer (Drapex 39, from Galata) | 3 |
| Heat stabilizer based on Ca/Zn (Mark CZ 149, from Galata) | 2 |

Figures in phr (phr=parts per hundred parts resin)

The ester mixtures were heated to 25° C. before being added. First the liquid constituents and then the pulverulent constituents were weighed out into a PE cup. The mixture was stirred manually with an ointment spatula in such a way that no unwetted powder was present any longer. The mixing beaker was then clamped into the clamping device of a dissolver stirrer. Before the stirrer was immersed into the mixture, the rotational speed was set to 1800 revolutions per minute. After switching on the stirrer, the mixture was stirred until the temperature on the digital display of the thermal sensor reached 30.0° C. This ensured that the plastisol was homogenized with a defined energy input. Thereafter, the plastisol was immediately equilibrated to 25.0° C. in a climate-controlled cabinet for further studies.

Example 9

Gelling Temperature of the Plastisols

The gelation characteristics of the plastisols were examined with a Physica MCR 101 in oscillation mode using a parallel plate analysis system (PP25), which was operated under shear stress control. An additional heating hood was connected to the system in order to achieve a homogeneous heat distribution and uniform sample temperature.

The following parameters were set:

Mode: Temperature gradient

| | |
|---|---|
| Start temperature | 25° C. |
| End temperature | 180° C. |
| Heating/cooling rate | 5° C./min |
| Oscillation frequency | 4-0.1 Hz logarithmic ramp |
| Frequency cycle omega: | 10 1/s |
| Number of measurement points: | 63 |
| Measurement point duration: | 0.5 min |
| Automatic gap adjustment F: | 0 N |
| Constant measurement point duration Gap width | 0.5 mm |

Analysis Procedure:

The spatula was used to apply a few grams of the plastisol to be analyzed, free from air bubbles, to the lower plate of the analysis system. In doing so, it was ensured that, after the analysis system had been assembled, it was possible for some plastisol to exude uniformly out of the analysis system (not more than about 6 mm in any direction). The heating hood was subsequently positioned over the sample and the analysis was started. What is called the complex viscosity of the plastisol was determined after 24 h (storage of the plastisol at 25° C. in a temperature control cabinet from Memmert) as a function of temperature.

The measure considered for the gelation was a significant increase in the complex viscosity. The value used for comparison was therefore the temperature on attainment of a plastisol viscosity of 1000 Pa·s.

TABLE 11

Gelling of the plastisols after 24 h, temperature in ° C. on attainment of a plastisol viscosity of $10^3$ Pa · s (in short: gelling temperature)

| Plasticizer | Gelling temperature [° C.] | Plasticizer | Gelling temperature [° C.] |
|---|---|---|---|
| DEHT | 87.3 | $C_8/C_9$ TM 7:38:55 | 106.3 |
| DINT | 109.2 | $C_8/C_9$ TM 20:46:34 | 100.3 |
| DPT | 69.8 | $C_8/C_9$ TM 38:48:14 | 96.0 |
| $C_4/C_8$ TM 3:27:70 | 82.4 | $C_8/C_{10}$ TM 7:38:55 | 126.7 |
| $C_4/C_8$ TM 11:45:24 | 77.6 | $C_8/C_{10}$ TM 17:49:34 | 118.9 |
| $C_4/C_8$ TM 26:50:24 | 72.7 | $C_8/C_{10}$ TM 35:48:17 | 109.0 |
| $C_5/C_9$ TM 3:27:70* | 91.9 | $C_4/C_9$ Blend 10:90 | 100.3 |
| $C_5/C_9$ TM 13:46:41* | 83.4 | $C_4/C_9$ Blend 20:80 | 88.0 |
| $C_5/C_9$ TM 24:51:25* | 79.8 | $C_4/C_9$ Blend 40:60 | 77.8 |
| $C_5/C_9$ TM 44:45:11* | 76.1 | $C_4/C_9$ Blend 60:40 | 71.4 |
| $C_5/C_{10}$ TM 53:40:7 | 76.1 | $C_4/C_9$ Blend 80:20 | 66.7 |
| $C_5/C_{10}$ TM 36:49:15 | 80.0 | $C_5/C_9$ Blend 80:20 | 73.2 |
| $C_5/C_{10}$ TM 18:50:32 | 86.4 | $C_5/C_9$ Blend 60:40 | 76.7 |
| $C_5/C_{13}$ TM 49:44:7 | 79.7 | $C_5/C_9$ Blend 40:60 | 81.8 |
| $C_5/C_{13}$ TM 29:52:19 | 90.0 | $C_5/C_9$ Blend 20:80 | 89.6 |
| $C_5/C_{13}$ TM 13:51:36 | 119.1 | | |

*inventive

For the ester mixtures of the invention, FIG. 1 plots the gelling temperature of the plastisol from Table 11 against the associated volatility of the film comprising the same ester mixture (from Example 11, Table 12).

Example 10

Production of Films of the Ester Mixtures.

The plastisols prepared in Example 8 were each processed to give films 1 mm thick.

For this purpose, first of all high-gloss release paper (from Sappi, Italy) was trimmed to a size of 30×44 cm and inserted in the clamping frame of the LTSV coating installation for the Mathis oven. The clamping frame was subsequently placed on the guide frame, the Mathis oven (model LTF) was adjusted to 200° C., and on reaching this temperature, the frame was preheated for 15 seconds. The knife coater was subsequently inserted into the clamping means and the knife gap was adjusted via preliminary experiments in such a way that the film thickness after the end of gelling was 1 mm (+/−0.05 mm). An adhesive strip was mounted on the leading edge of the paper in order to catch excess paste. The paste was then applied in front of the coating knife, and spread by drawing of the guide frame with the coating knife over the clamped released paper (at a speed of about 3 m/min). The coating knife was then removed and the adhesive strip with the excess paste was taken off. The melting roll was then lowered and the clamping frame was moved into the oven. After gelling had taken place (2 minutes at 200° C.), the frame was moved out of the oven again and, after cooling, the film was removed from the paper.

3 circles of 10 cm² per formula under test were punched from the film. Additionally, the circles were cut into radially with scissors (2 cuts each of 5 mm). The circles were conditioned for half an hour in a desiccator (packed with orange KC drying pearls) then weighed.

Example 11

Loss of Mass on Activated Carbon Storage for the Films from Example 10

Tin cans (1 l, tall shape) were punctured in the lid in order that exchange of pressure could take place. The base of the tin cans was covered with 120 ml of activated carbon. The activated carbon used in this test (No. 774408 from Roth) was dried beforehand in an evaporator boat in a drying cabinet at 100+/−1° C. for 6 hours beforehand, and used after brief cooling. The first sample circle was placed onto the middle of the activated carbon. A further 120 ml of activated carbon were placed onto the sample circle. In total, the tin cans were filled with 480 ml of activated carbon and 3 sample circles in layers. The lid of the tin cans was placed onto the cans without pressure.

The filled tin cans were stored in a temperature control cabinet at 100+/−1° C. for 3 days. After the storage, the activated carbon was removed from the circles by means of an analysis brush, and the circles were stored in a desiccator for 30 minutes for cooling and then weighed.

After the weighing, the sample circles were layered again with activated carbon in the tin cans. For this purpose, it was ensured that the sample circles were again assigned to the same activated carbon and the same can. The cans were placed in the temperature control cabinet again. After a total of 7 days, the samples were then weighed again as already described.

The percentage change in mass of each sample circle was calculated, and the mean over the 3 circles for each formulation was calculated.

TABLE 12

Loss of mass on activated carbon storage in mass % (volatility)

| Plasticizer | Volatility [mass %] | Plasticizer | Volatility [mass %] |
|---|---|---|---|
| DEHT | 10.4 | $C_8/C_9$ TM 7:38:55 | 5.3 |
| DINT | 5.4 | $C_8/C_9$ TM 20:46:31 | 5.9 |
| DPT | 26.2 | $C_8/C_9$ TM 38:48:14 | 6.9 |
| $C_4/C_8$ TM 3:27:70 | 16.1 | $C_8/C_{10}$ TM 7:38:55 | 3.5 |
| $C_4/C_8$ TM 11:45:24 | 19.5 | $C_8/C_{10}$ TM 17:49:34 | 4.8 |
| $C_4/C_8$ TM 26:50:24 | 23.7 | $C_8/C_{10}$ TM 35:48:17 | 5.4 |
| $C_5/C_9$ TM 3:27:70* | 8.1 | $C_4/C_9$ Blend 10:90 | 7.2 |
| $C_5/C_9$ TM 13:46:41* | 11.0 | $C_4/C_9$ Blend 20:80 | 10.2 |
| $C_5/C_9$ TM 24:51:25* | 15.3 | $C_4/C_9$ Blend 40:60 | 16.2 |
| $C_5/C_9$ TM 44:45:11* | 20.8 | $C_4/C_9$ Blend 60:40 | 22.0 |
| $C_5/C_{10}$ TM 53:40:7 | 22.3 | $C_4/C_9$ Blend 80:20 | 27.1 |
| $C_5/C_{10}$ TM 36:49:15 | 20.3 | $C_5/C_9$ Blend 80:20 | 24.7 |
| $C_5/C_{10}$ TM 18:50:32 | 15.5 | $C_5/C_9$ Blend 60:40 | 20.7 |
| $C_5/C_{13}$ TM 49:44:7 | 18.4 | $C_5/C_9$ Blend 40:60 | 15.5 |
| $C_5/C_{13}$ TM 29:52:19 | 11.8 | $C_5/C_9$ Blend 20:80 | 10.0 |
| $C_5/C_{13}$ TM 13:51:36 | 7.2 | | |

*inventive

For the ester mixtures of the invention, FIG. 1 plots the gelling temperature of plastisol from Table 11 of Example 9 against the associated volatility of the film comprising the same ester mixture (from Table 12).

Figure 2:
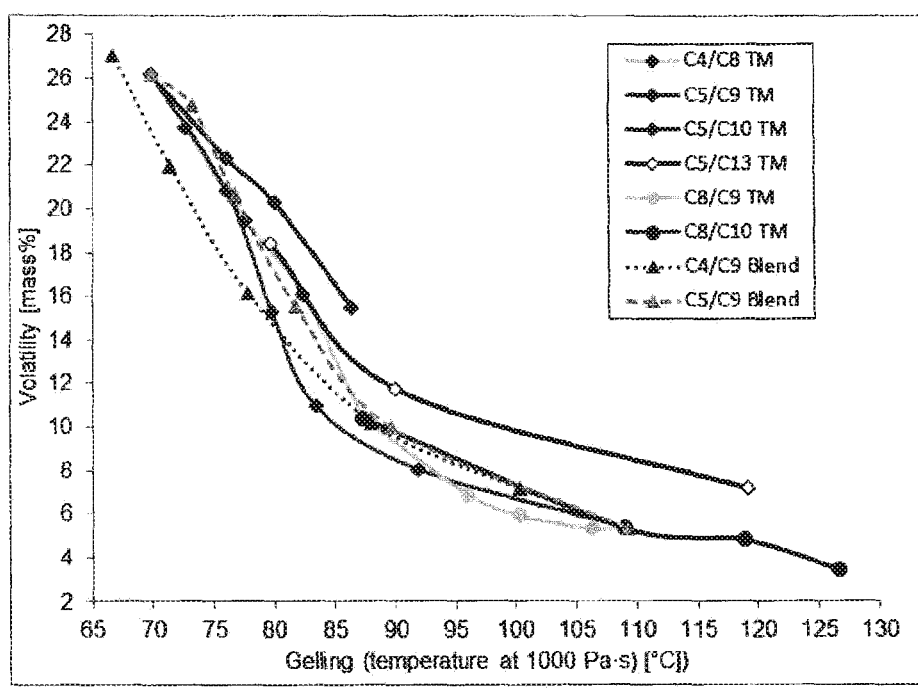
FIG. 2 shows the gelling temperature against volatility for ester mixtures according to the present invention and comparative substances.

For all of the plasticizer systems included in Table 9, FIG. 2 shows a plot of the gelling temperature against the volatility. From this plot it is evident that products (plastisols/films) of the inventive ester mixtures, in comparison to the other polymer-compatible, SVOC-free plasticizer systems, have lower gelling temperatures and at the same time lower volatilities and therefore, relative to these plasticizer systems, exhibit improved properties for processing and application. Below gelling temperatures of about 80° C., exclusively mixtures of dibutyl terephthalate and diisononyl terephthalate exhibit a better balance of volatility and gelling properties than the inventive mixtures. However, these $C_4$ alcohol radical-containing mixtures are subject to the restrictions already elucidated in the description, since dibutyl terephthalate is classed as an SVOC component and hence does not constitute a viable alternative to, let alone an improvement over, the inventive mixtures. Above gelling temperatures of about 94° C., according to FIG. 2, an ester mixture of $C_8$ and $C_9$ alkyl radicals appears to have a better balance of volatility and gelling properties than the inventive mixtures. As will be shown below (Example 12), however, the ester mixtures of $C_8$ and $C_9$ alkyl radicals exhibit poor compatibility with polymers and a relatively low efficiency (see Example 14 in relation to the Shore hardness).

Example 12

Determination of the Compatibility of the Mixtures with Polymers by the Loop Test (in Accordance with ASTM D3291)

From the PVC films of Example 10, three rectangles (5×1 cm) per sample were cut out. The rectangles were annotated on the reverse.

The specimens were bent 180° by hand and placed in a test rail. The film rectangles were bent in the top face direction. A little air is left (about 0.5 cm) between the specimens, so that the samples do not come into contact with one another. The ends of the bent rectangles still show to some extent from the rail.

The Loop Test rails were stored in a conditioned chamber (air temperature 22° C.+/−1° C. atmospheric humidity 50%+/−5%).

After 1, 7 and 14 days, the corresponding rectangles were taken from the rail and bent by hand into the opposite direction. The point at which the specimens were most severely bent was pressed in each case over a piece of cigarette paper, and the exudation behavior of the plasticizer under test was assessed via the size of the spot formed on the cigarette paper, as follows:

0=no exudation
0.5=very little exudation
1=little exudation
2=moderate exudation
3=severe exudation
>3=very severe exudation

TABLE 13

Assessment of the exudation behavior

| Plasticizer | Evaluation | | |
|---|---|---|---|
| | after 1 day | after 7 days | after 14 days |
| DEHT | 0 | 0 | 0 |
| DINT | 0.5 | 2.5 | 2 |
| DPT | 0 | 0 | 0 |
| $C_4/C_8$ TM 3:27:70 | 0 | 0 | 0 |
| $C_4/C_8$ TM 11:45:24 | 0 | 0 | 0 |
| $C_4/C_8$ TM 26:50:24 | 0 | 0 | 0 |
| $C_5/C_9$ TM 3:27:70* | 0.5 | 1 | 1 |
| $C_5/C_9$ TM 13:46:41* | 0 | 0 | 0 |
| $C_5/C_9$ TM 24:51:25* | 0 | 0 | 0 |
| $C_5/C_9$ TM 44:45:11* | 0 | 0 | 0 |
| $C_5/C_9$ TM 53:40:7 | 0 | 0 | 0 |
| $C_5/C_{10}$ TM 36:49:15 | 0 | 0 | 0 |
| $C_5/C_{10}$ TM 18:50:32 | 0 | 0 | 0 |
| $C_5/C_{13}$ TM 49:44:7 | 0 | 0 | 0 |
| $C_5/C_{13}$ TM 29:52:19 | 0 | 0.5 | 0.5 |
| $C_5/C_{13}$ TM 13:51:36 | 0.5 | 0.5 | 1 |
| $C_8/C_9$ TM 7:38:55 | 0 | 1 | 1 |
| $C_8/C_9$ TM 20:46:34 | 0 | 0.5 | 0 |
| $C_8/C_9$ TM 38:48:14 | 0 | 0.5 | 0 |
| $C_8/C_{10}$ TM 7:38:55 | 2 | 2.5 | 2.5 |
| $C_8/C_{10}$ TM 17:49:34 | 1.5 | 2 | 2 |
| $C_8/C_{10}$ TM 35:48:17 | 1 | 1.5 | 1.5 |
| $C_4/C_9$ Blend 10:90 | 0 | 0.5 | 0.5 |
| $C_4/C_9$ Blend 20:80 | 0 | 0.5 | 0 |
| $C_4/C_9$ Blend 40:60 | 0 | 0 | 0 |

TABLE 13-continued

Assessment of the exudation behavior

| | Evaluation | | |
|---|---|---|---|
| Plasticizer | after 1 day | after 7 days | after 14 days |
| $C_4/C_9$ Blend 60:40 | 0 | 0 | 0 |
| $C_4/C_9$ Blend 80:20 | 0 | 0 | 0 |
| $C_5/C_9$ Blend 80:20 | 0 | 0 | 0 |
| $C_5/C_9$ Blend 60:40 | 0 | 0 | 0 |
| $C_5/C_9$ Blend 40:60 | 0 | 0 | 0 |
| $C_5/C_9$ Blend 20:80 | 0 | 1 | 0.5 |

*inventive

The evaluations compiled in Table 13 show that ester mixtures which contain $C_8$ and $C_{10}$ alcohol radicals or $C_8$ and $C_9$ alcohol radicals or $C_5$ and $C_{13}$, alcohol radicals are of poor compatibility with polymers, in the present case PVC, if significant amounts of the long-chain alcohol radical are present. Such systems are therefore not suitable for "performance-oriented" processing with polymers.

Example 13

Change in Mass of Specimens after Water Storage

The ageing resistance under different ambient conditions is a further key quality criterion for plasticizers. Particularly the behavior with respect to water (water absorption and leaching of formula constituents) and with respect to elevated temperatures (evaporation of formula constituents and thermal ageing) offers an insight into the ageing resistance.

If a plastics article absorbs water substantially, this results in a change both in its physical properties and also in its optical properties (e.g. cloudy). A high water absorption is accordingly generally undesirable. The leaching behavior is an additional criterion for the permanence of the formulation constituents under conditions of use. This applies in particular to stabilizers, plasticizers and/or constituents thereof, since a reduction in the concentration of these formulation constituents in the plastic article can both adversely affect the material properties and also dramatically reduce the service life.

For the determination of the water resistance, films as produced in Example 10 were used. Circular films of 3 cm diameter were cut out as test samples. Prior to storage in water, the test samples were stored for 24 hours at 25° C. in a desiccator furnished with drying agent (KC drying beads, BASF SE). The starting weight (initial mass) was determined to an accuracy of 0.1 mg with an analytical balance. The test specimens were then stored in a shaker bath (of the WNB 22 type with "CDP" Peltier cooler; from Memmert GmbH) filled with fully demineralized (DI) water, at a temperature of 30° C., for 7 days under the water surface with sample holders while being continuously agitated. Following storage, the circles were removed from the water bath, dried and weighed (=weight after 7 days). The water absorption was calculated from the difference relative to the initial mass. After the final weighing, the test specimens were again stored for 24 hours at 25° C. in a desiccator furnished with drying agent (KC drying beads) and then weighed again (final weight=weight after drying). The percentage loss of mass as a result of water storage (corresponding to leaching losses) was calculated from the difference relative to the initial mass prior to water storage.

TABLE 14

Change in the mass of specimens after water storage

| Plasticizer | Change in mass after drying | Plasticizer | Change in mass after drying |
|---|---|---|---|
| DEHT | 0.06 | $C_8/C_9$ TM 7:38:55 | −0.06 |
| DINT | 0.07 | $C_8/C_9$ TM 20:46:34 | −0.04 |
| DPT | −0.02 | $C_8/C_9$ TM 38:48:14 | −0.03 |
| $C_4/C_8$ TM 3:27:70 | −0.02 | $C_8/C_{10}$ TM 7:38:55 | 0.08 |
| $C_4/C_8$ TM 11:45:24 | −0.12 | $C_8/C_{10}$ TM 17:49:34 | 0.08 |
| $C_4/C_8$ TM 26:50:24 | −0.23 | $C_8/C_{10}$ TM 35:48:17 | 0.06 |
| $C_5/C_9$ TM 3:27:70* | 0.06 | $C_4/C_9$ Blend 10:90 | −0.10 |
| $C_5/C_9$ TM 13:46:41* | 0.03 | $C_4/C_9$ Blend 20:80 | −0.17 |
| $C_5/C_9$ TM 24:51:25* | 0.05 | $C_4/C_9$ Blend 40:60 | −0.35 |
| $C_5/C_9$ TM 44:45:11* | 0.01 | $C_4/C_9$ Blend 60:40 | −0.49 |
| $C_5/C_{10}$ TM 53:40:7 | −0.06 | $C_4/C_9$ Blend 80:20 | −0.65 |
| $C_5/C_{10}$ TM 36:49:15 | −0.04 | $C_5/C_9$ Blend 80:20 | −0.04 |
| $C_5/C_{10}$ TM 18:50:32 | −0.03 | $C_5/C_9$ Blend 60:40 | −0.02 |
| $C_5/C_{13}$ TM 49:44:7 | −0.10 | $C_5/C_9$ Blend 40:60 | 0.00 |
| $C_5/C_{13}$ TM 29:52:19 | −0.09 | $C_5/C_9$ Blend 20:80 | 0.00 |
| $C_5/C_{13}$ TM 13:51:36 | −0.45 | | |

*inventive

The changes in mass summarized in Table 14 show that ester mixtures containing $C_4$ alcohol radicals exhibit greater losses of mass on water storage. The inventive mixtures, in contrast, exhibit negligible changes in mass after storage of the test specimens in water. Good resistance during water storage is important particularly for the use of plasticizers in hoses and tubes and in outdoor applications.

Example 14

Determination of the Efficiency of Mixtures (Shore A Hardness of the Plasticized PVC Samples)

Shore hardness is a measure of the softness of a sample. The further a standardized needle can penetrate into the sample in a particular measurement period, the lower the measured value. The plasticizer having the highest efficiency for the same amount of plasticizer gives the lowest Shore hardness value. Since, in practice, formulations are frequently adjusted or optimized to a certain Shore hardness, very efficient plasticizers can accordingly be reduced to a particular proportion in the formulation, which leads to a reduction in costs for the processor.

For the determination of the Shore hardnesses, the plastisols produced in Example 8 were poured into circular brass casting moulds having a diameter of 42 mm (initial weight: 20.0 g). The pastes were then gelated in the moulds in an air circulation drying cabinet at 200° C. for 30 min, cooled and then removed, and stored in a climate-controlled cabinet (25° C.) for at least 24 hours prior to the measurement. The slice thickness was about 12 mm.

The hardness measurements were conducted to DIN 53 505 using a Shore A measuring instrument from Zwick-Roell; the measurement was read off after 3 seconds in each case. For each test specimen, measurements were conducted at three different positions, and the mean was determined.

TABLE 15

Shore A hardness of test specimens comprising plasticizers listed in Table 9

| Plasticizer | Shore A hardness | Plasticizer | Shore A hardness |
|---|---|---|---|
| DEHT | 82 | $C_8/C_9$ TM 7:38:55 | 87 |
| DINT | 88 | $C_8/C_9$ TM 20:46:34 | 86 |

TABLE 15-continued

Shore A hardness of test specimens comprising plasticizers listed in Table 9

| Plasticizer | Shore A hardness | Plasticizer | Shore A hardness |
| --- | --- | --- | --- |
| DPT | 72 | $C_8/C_9$ TM 38:48:14 | 85 |
| $C_4/C_8$ TM 3:27:70 | 80 | $C_8/C_{10}$ TM 7:38:55 | 92 |
| $C_4/C_8$ TM 11:45:24 | 77 | $C_8/C_{10}$ TM 17:49:34 | 90 |
| $C_4/C_8$ TM 26:50:24 | 74 | $C_8/C_{10}$ TM 35:48:17 | 88 |
| $C_5/C_9$ TM 3:27:70* | 84 | $C_4/C_9$ Blend 10:90 | 85 |
| $C_5/C_9$ TM 13:46:41* | 82 | $C_4/C_9$ Blend 20:80 | 81 |
| $C_5/C_9$ TM 24:51:25* | 80 | $C_4/C_9$ Blend 40:60 | 77 |
| $C_5/C_9$ TM 44:45:11* | 77 | $C_4/C_9$ Blend 60:40 | 72 |
| $C_5/C_{10}$ TM 53:40:7 | 75 | $C_4/C_9$ Blend 80:20 | 68 |
| $C_5/C_{10}$ TM 36:49:15 | 78 | $C_5/C_9$ Blend 80:20 | 75 |
| $C_5/C_{10}$ TM 18:50:32 | 82 | $C_5/C_9$ Blend 60:40 | 77 |
| $C_5/C_{13}$ TM 49:44:7 | 79 | $C_5/C_9$ Blend 40:60 | 79 |
| $C_5/C_{13}$ TM 29:52:19 | 85 | $C_5/C_9$ Blend 20:80 | 83 |
| $C_5/C_{13}$ TM 13:51:36 | 91 | | |

*inventive

Test specimens of the inventive mixtures show a lower Shore A hardness and hence a better plasticizer efficiency than test specimens with ester mixtures comprising $C_8$ and $C_9$ alcohol radicals and, respectively, $C_9$ and $C_{10}$ alcohol radicals, this leading to lower formula costs for the inventive mixtures.

European patent application EP15155562 filed Feb. 18, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A composition, comprising:

polyvinyl chloride; and 30-100 parts by weight of a mixture, based on 100 parts of the polyvinyl chloride;

wherein the mixture comprises a terephthalic diester of each of the formulae I, II and III,

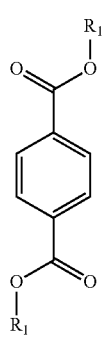

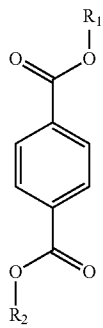

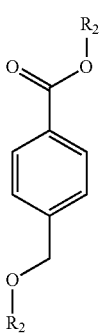

wherein
$R_1$ is an alkyl radical having 5 carbon atoms, and
$R_2$ is an alkyl radical having 9 carbon atoms; and
wherein the mixture comprises
3-44 mol % of the ester of formula I,
27-51 mol % of the ester of formula II, and
11-70 mol % of the ester of formula III, each based on the entirety of the esters I, II and III.

2. The composition of claim 1, wherein in the formulae I, II and III, $R_1$ is selected from the group consisting of 2-methylbutyl, 3-methylbutyl, n-pentyl and isopentyl radicals and $R_2$ is selected from the group consisting of nonyl, n-nonyl and isononyl radicals.

3. The composition of claim 1, wherein the mixture comprises
13-24 mol % of the ester of formula I,
46-51 mol % of the ester of formula II, and
25-41 mol % of the ester of formula III, each based on the entirety of the esters I, II and III.

4. The composition of claim 1, wherein the mixture comprises
11-29 mol % of the ester of formula I,
45-51 mol % of the ester of formula II, and
21-44 mol % of the ester of formula III, each based on the entirety of the esters I, II and III.

5. The composition of claim 1, wherein the mixture comprises less than 3 mol % of terephthalic diesters which do not fall within the definition of the terephthalic diesters of formulae I, II and III.

6. The composition of claim 1, further comprising an epoxidized soybean oil and a heat stabilizer.

7. The composition of claim 1, which is a plastisol.

8. An adhesive, sealant, coating material, paint, ink, plastisol, foam, synthetic leather, floorcovering, roofing membrane, underbody protection, fabric coating, cable, wire insulation, hose, extruded article, film, automotive interior article, wallcovering, liquid ink, toy, contact sheet, food packaging or medical article, comprising:
the composition of claim 1.

* * * * *